(12) United States Patent
Haight et al.

(10) Patent No.: US 8,389,890 B2
(45) Date of Patent: *Mar. 5, 2013

(54) METHOD FOR MINIMIZING SAMPLE DAMAGE DURING THE ABLATION OF A FIRST BIOLOGICAL MATERIAL DISPOSED ON A SECOND BIOLOGICAL MATERIAL USING A FOCUSED ULTRASHORT PULSED LASER BEAM WHEREIN THE SLOPE OF FLUENCE BREAKDOWN IS A FUNCTION OF THE PULSE WIDTH

(75) Inventors: Richard Alan Haight, Mahopac, NY (US); Peter P. Longo, Hopewell Junction, NY (US); Daniel Peter Morris, Purchase, NY (US); Alfred Wagner, Brewster, NY (US)

(73) Assignee: International Business Machines Corporation, Armonk, NY (US)

( * ) Notice: Subject to any disclaimer, the term of this patent is extended or adjusted under 35 U.S.C. 154(b) by 400 days.

This patent is subject to a terminal disclaimer.

(21) Appl. No.: 12/545,216

(22) Filed: Aug. 21, 2009

(65) Prior Publication Data

US 2010/0006550 A1    Jan. 14, 2010

Related U.S. Application Data

(60) Division of application No. 09/933,461, filed on Aug. 20, 2001, now Pat. No. 7,649,153, which is a continuation-in-part of application No. 09/210,226, filed on Dec. 11, 1998, now Pat. No. 6,333,485.

(51) Int. Cl.
*B23K 26/36* (2006.01)
*B23K 26/06* (2006.01)

(52) U.S. Cl. ..................................... 219/121.69; 606/10

(58) Field of Classification Search ............. 219/121.67, 219/121.68, 121.69, 121.71, 121.72, 121.73, 219/121.75, 121.7, 121.83, 121.78, 121.79, 219/121.8, 121.81; 606/10, 11, 12; 372/25; 216/65; 378/122; 438/940
See application file for complete search history.

(56) References Cited

U.S. PATENT DOCUMENTS 3,865,114 A * 2/1975 Sharon ..................... 219/121.83
(Continued)

FOREIGN PATENT DOCUMENTS

JP    1-233081 A  *  9/1989
JP    3-66488 A   *  3/1991

*Primary Examiner* — Geoffrey S Evans
(74) *Attorney, Agent, or Firm* — Daniel P. Morris

(57) ABSTRACT

In one aspect the invention provides a method for laser induced breakdown of a material with a pulsed laser beam where the material is characterized by a relationship of fluence breakdown threshold (Fth) versus laser beam pulse width (T) that exhibits an abrupt, rapid, and distinct change or at least a clearly detectable and distinct change in slope at a predetermined laser pulse width value. The method comprises generating a beam of laser pulses in which each pulse has a pulse width equal to or less than the predetermined laser pulse width value. The beam is focused above the surface of a material where laser induced breakdown is desired. The region of least confusion (minimum beam waist or average spot size) is above the surface of the material in which laser induced breakdown is desired since the intensity of the beam falls off in the forward direction, preferably the region of the beam at or within the surface is between the region of least confusion and sufficient to remove material and the minimum intensity necessary for laser induced breakdown of the material to be removed, most preferably the region of minimum intensity is disposed at the surface of the material to be removed. The beam may be used in combination with a mask in the beam path. The beam or mask may be moved in the x, y, and Z directions to produce desired features. The technique can produce features smaller than the spot size and Rayleigh range due to enhanced damage threshold accuracy in the short pulse regime.

73 Claims, 14 Drawing Sheets

U.S. PATENT DOCUMENTS

| | | | |
|---|---|---|---|
| 4,762,514 A * | 8/1988 | Yoshida | 219/121.69 |
| 4,894,115 A * | 1/1990 | Eichelberger et al. | 219/121.69 |
| 4,940,881 A * | 7/1990 | Sheets | 219/121.69 |
| 4,943,700 A * | 7/1990 | Hughes et al. | 219/121.67 |
| 5,053,171 A * | 10/1991 | Portney et al. | 219/121.69 |
| 5,160,823 A * | 11/1992 | Bennin et al. | 219/121.68 |
| 5,179,262 A * | 1/1993 | Portney et al. | 219/121.68 |
| 5,250,785 A * | 10/1993 | Blommel et al. | 219/121.67 |
| 5,508,489 A * | 4/1996 | Benda et al. | 219/121.76 |
| 5,656,186 A * | 8/1997 | Mourou et al. | 219/121.69 |
| 5,662,762 A * | 9/1997 | Ranalli | 219/121.69 |
| 5,728,994 A * | 3/1998 | Hutton | 219/121.69 |
| 5,800,625 A * | 9/1998 | Engelsberg et al. | 134/1 |
| 5,916,460 A * | 6/1999 | Imoto et al. | 219/121.67 |
| 6,008,467 A * | 12/1999 | Tsunetomo et al. | 219/121.69 |
| 6,333,485 B1 * | 12/2001 | Haight et al. | 219/121.68 |
| 7,649,153 B2 * | 1/2010 | Haight et al. | 219/121.69 |

* cited by examiner

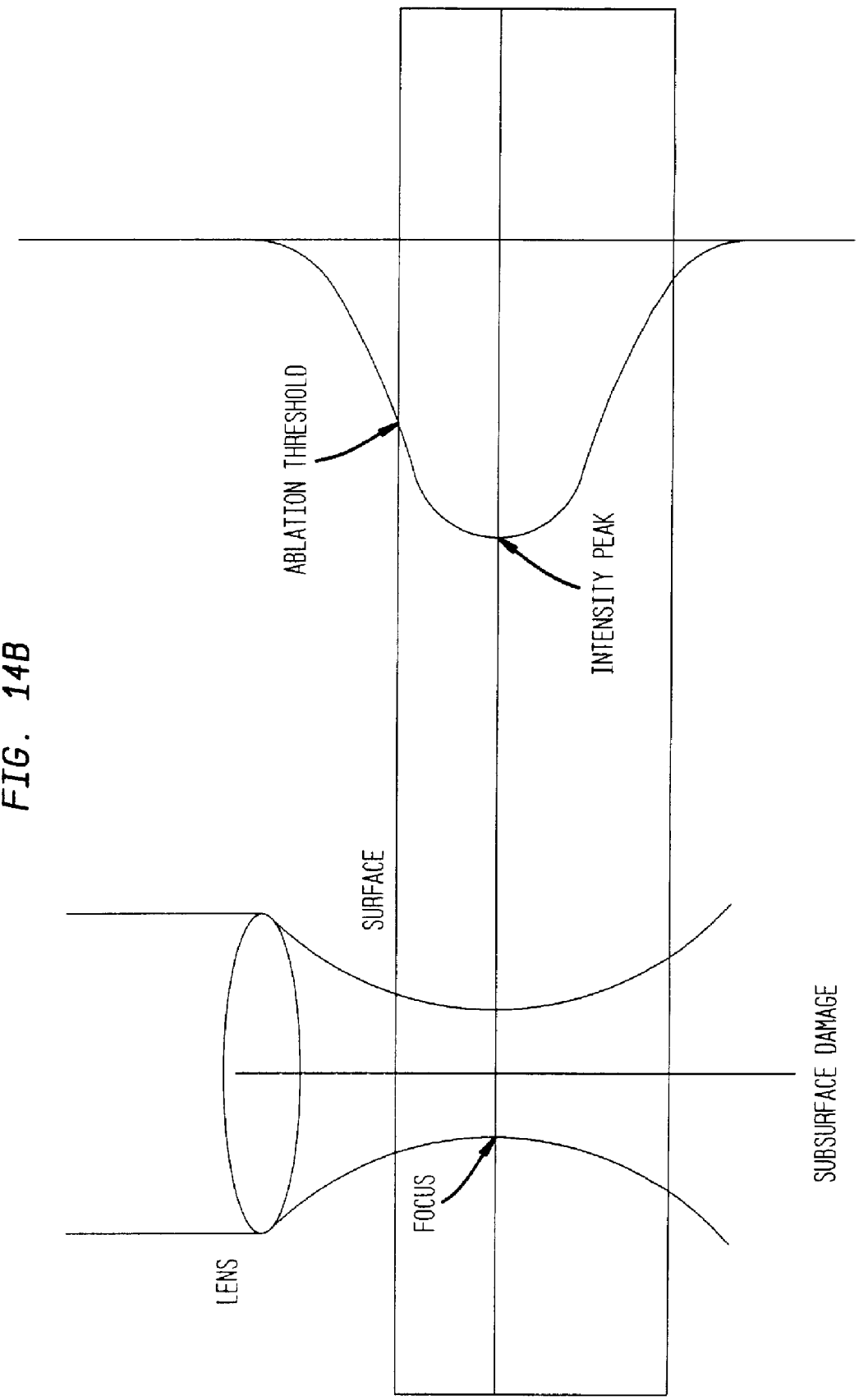

METHOD FOR MINIMIZING SAMPLE DAMAGE DURING THE ABLATION OF A FIRST BIOLOGICAL MATERIAL DISPOSED ON A SECOND BIOLOGICAL MATERIAL USING A FOCUSED ULTRASHORT PULSED LASER BEAM WHEREIN THE SLOPE OF FLUENCE BREAKDOWN IS A FUNCTION OF THE PULSE WIDTH

This application is a division of U.S. application Ser. No. 09/933,461, filed on Aug. 20, 2001 now issued as U.S. Pat. No. 7,649,153, which is a Continuation-in-Part of U.S. application Ser. No. 09/210,226, filed on Dec. 11, 2001 now issued as U.S. Pat. No. 6,333,485.

FIELD OF THE INVENTION

This invention relates generally to methods utilizing lasers for modifying internal and external surfaces of material such as by ablation or changing properties in structure of materials. This invention may be used for a variety of materials.

BACKGROUND OF THE INVENTION

Laser induced breakdown of a material causes chemical and physical changes, chemical and physical breakdown, disintegration, ablation, and vaporization. Lasers provide good control for procedures which require precision such as inscribing a micro pattern. Pulsed rather than continuous beams are more effective for many procedures, including medical procedures. A pulsed laser beam comprises bursts or pulses of light which are of very short duration, for example, on the order of 10 nanoseconds in duration or less. Typically, these pulses are separated by periods of quiescence. The peak power of each pulse is relatively high often on the order of gigawatts and capable of intensity on the order of 1013 w/cm2. Although the laser beam is focused onto an area having a selected diameter, the effect of the beam extends beyond the focused area or spot to adversely affect peripheral areas adjacent to the spot. Sometimes the peripheral area affected is several times greater than the spot itself. This presents a problem, particularly where tissue is affected in a medical procedure. In the field of laser machining, current lasers using nanosecond pulses cannot produce features with a high degree of precision and control, particularly when nonabsorptive wavelengths are used.

It is a general object to provide a method to localize laser induced breakdown. Another object is to provide a method to induce breakdown in a preselected pattern in a material or on a material.

U.S. Pat. No. 5,656,186 to Mourou et al. is directed to a method for laser-induced breakdown. The teaching of Mourou et al. requires that the laser beam be focused to a point at or beneath the surface from which material is to be removed. Applicants have discovered that it is undesirable to focus at or beneath the surface since this results in undesired damage beneath the surface, in particular to the substrate (or underlayer) on which the material that is to be removed is disposed. This is particularly a problem where the underlayer is very sensitive to the laser light and/or can be easily damaged by the laser light. Applicants have unexpectedly discovered that the light source should be focused above the surface to be removed toward this undesired change.

SUMMARY OF THE INVENTION

In one aspect the invention provides a method for laser induced breakdown of a material with a pulsed laser beam where the material is characterized by a relationship of fluence breakdown threshold (Fth) versus laser beam pulse width (T) that exhibits an abrupt, rapid, and distinct change or at least a clearly detectable and distinct change in slope at a predetermined laser pulse width value. The method generating a beam of laser pulses in which each pulse has a pulse width equal to or less than the predetermined laser pulse width value. The beam is focused to a point above the surface of a material where laser induced breakdown is desired. The beam is focused to have the region of least confusion above the surface of a material where laser-induced breakdown is desired.

In one aspect, the invention may be understood by further defining the predetermined laser pulse width as follows: the relationship between fluence breakdown threshold and laser pulse defines a curve having a first portion spanning a range of relatively long (high) pulse width where fluence breakdown threshold (Fth) varies with the square root of pulse width (T1/2). The curve has a second portion spanning a range of short (low) pulse width relative to the first portion. The proportionality between fluence breakdown threshold and pulse width differ in the first and second portions of the curve and the predetermined pulse width is that point along the curve between its first and second portions. In other words, the predetermined pulse width is the point where the Fth versus .tau.p relationship no longer applies, and, of course, it does not apply for pulse widths shorter than the predetermined pulse width.

The scaling of fluence breakdown threshold (Fth) as a function of pulse width (T) is expressed as Fth proportional to the square root of T½) is demonstrated in the pulse width regime to the nanosecond range. The invention provides methods for operating in pulse widths to the picosecond and femtosecond regime where we have found that the breakdown threshold (Fth) does not vary with the square root of pulse width (T1/2).

Pulse width duration from nanosecond down to the femtosecond range is accomplished by generating a short optical pulse having a predetermined duration from an optical oscillator. Next the short optical pulse is stretched in time by a factor of between about 500 and 10,000 to produce a timed stretched optical pulse to be amplified. Then, the time stretched optical pulse is amplified in a solid state amplifying media. This includes combining the time stretched optical pulse with an optical pulse generated by a second laser used to pump the solid state amplifying media. The amplified pulse is then recompressed back to its original pulse duration.

In one embodiment, a laser oscillator generates a very short pulse on the order of 10 to 100 femtoseconds at a relatively low energy, on the order of 0.001 to 10 nanojoules. Then, it is stretched to approximately 100 picoseconds to 1 nanosecond and 0.001 to 10 nanojoules. Then, it is amplified to typically on the order of 0.001 to 1,000 millijoules and 100 picoseconds to 1 nanosecond and then recompressed. In its final state it is 10 to 200 femtoseconds and 0.001 to 1,000 millijoules. Although the system for generating the pulse may vary, it is preferred that the laser medium be sapphire which includes a titanium impurity responsible for the lasing action.

In one aspect, the method of the invention provides a laser beam which defines a spot that has a lateral gaussian profile characterized in that fluence at or near the center of the beam spot is greater than the threshold fluence whereby the laser induced breakdown is ablation of an area within the spot. The maximum intensity is at the very center of the beam waist. The beam waist is the point in the beam where wave-front becomes a perfect plane; that is, its radius of curvature is infinite. This center is at radius R=0 in the x-y axis and along the Z axis, Z=0. This makes it possible to damage material in a very small volume Z=0, R=0. Thus it is possible to make features smaller than spot size in the x-y focal plane and smaller than the Rayleigh range (depth of focus) in the Z axis. It is preferred that the pulse width duration be in the femtosecond range although pulse duration of higher value may be used so long as the value is less than the pulse width defined by an abrupt or discernable change in slope of fluence breakdown threshold versus laser beam pulse width.

In another aspect, a diaphragm, disk, or mask is placed in the path of the beam to block at least a portion of the beam to cause the beam to assume a desired geometric configuration. In still further aspects, desired beam configurations are achieved by varying beam spot size or through Fourier Transform (FT) pulse shaping to cause a special frequency distribution to provide a geometric shape.

It is preferred that the beam have an energy in the range of 10 nJ (nanojoules) to 1 millijoule and that the beam have a fluence in the range of 0.1 J/cm2 to 100 J/cm2 (joules per centimeter square). It is preferred that the wavelength be in a range of 200 nm (nanometers) to 1 urn (micron).

Advantageously, the invention provides a new method for determining the optimum pulse width duration regime for a specific material and a procedure for using such regime to produce a precisely configured cut or void in or on a material. For a given material the regime is reproducible by the method of the invention. Advantageously, very high intensity results from the method with a modest amount of energy and the spot size can be very small. Damage to adjoining area is minimized which is particularly important to human and animal tissue.

These and other object features and advantages of the invention will be become apparent from the following description of the preferred embodiments, claims, and accompanying drawings.

BRIEF DESCRIPTION OF THE DRAWINGS

FIG. 14b shows a light source focused beneath the surface of the layer to be ablated.

DETAILED DESCRIPTION

Figure 1:
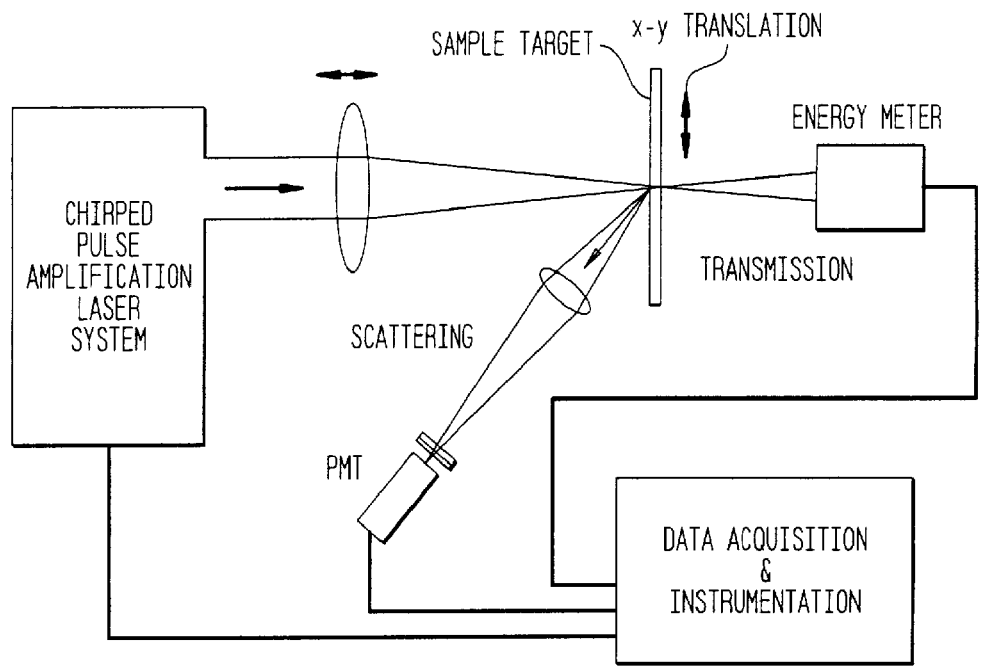
FIG. 1 is a schematic representation of a laser induced breakdown experimental system which includes a chirped pulse amplification laser system and means for detecting scattered and transmitted energy. If the sample is transparent, then transmitted energy can also be measured.

Pulses of light emitted by a laser are capable of removing material from a sample. Typically, the light is focused onto the surface of the sample to both 1) increase the intensity of the light and 2) localize the region of material removal. We have found that it is particularly advantageous to focus the laser beam above the surface of the material to be ablated, rather than focusing at or below the surface. In any situation where material must be removed from the surface without risking damage or ablation of the underlying substrate, our focusing technique is crucial. By focusing above the surface, the maximum intensity of laser light occurs away from the sample. The light intensity then decreases monotonically as the laser beam moves toward and into the sample (see FIG. 14a). This procedure ensures that the laser intensity inside the sample is always less than the intensity at the surface of the material to be ablated. Since it is often necessary to confine ablation and potential damage to the surface of the sample, focusing above the plane of the sample and then adjusting the intensity of the light to the minimum necessary for ablation ensures that no region beneath the surface of the sample will be ablated or damaged.

Our focusing technique is particularly critical when ultrashort (<10 psec) pulsed lasers are utilized for ablation. Since ultrashort pulsed laser ablation is non-thermal, the ablated region is limited to the spatial extent of the focused laser light. Therefore, to eliminate ablation and damage to the underlying substrate, it is essential to ensure that the peak light intensity occurs outside the sample. Our method ensures this. Our technique contrasts significantly with laser ablation in which the objective is to remove large quantities of material without regard to inflicting damage to the underlying substrate. In this case, by focusing the laser beam at or below the surface the laser intensity peaks inside the material (see FIG. 14b). This results in the maximum ablation efficiency, a desirable characteristic when drilling a simple hole without regard to substrate damage.

The following are examples which illustrate the benefit of focusing the laser beam above the surface of the sample to avoid sample damage. In the course of developing a tool to ablate chromium defects on a quartz photomask, we focused a femtosecond pulsed laser beam onto the surface of the chromium. We found that it was difficult to avoid damaging the underlying quartz substrate using this approach, since the normal variation in focus which typically occurred would often cause the laser beam to be focused inside the quartz. When the beam focus occurred in the quartz, the laser intensity was sufficient to damage the quartz rendering the photomask unusable. However, by focusing the laser beam above the chromium surface, we could adjust the laser intensity so that the Cr was ablated while the quartz was unaffected. Similarly, in removing unwanted biological tissue such as a tumor from an organ, focusing the laser beam above the surface of the tumor results in its removal without damaging the underlying tissue. Consider a tumor attached to the retina of the eye. Focusing a pulsed laser at or below the surface of the tumor can result in a maximum laser intensity in the retina rather than the tumor. As the tumor is slowly ablated by the laser beam, the laser intensity at or below the retina will be greater than the laser intensity at the tumor if the laser is focused at or below the surface of the tumor. Focusing above the surface of the tumor ensures that the laser intensity is as small as possible at the retina and decreases with increasing depth into the retina. This minimizes inadvertent damage to the retina.

Figure 2:
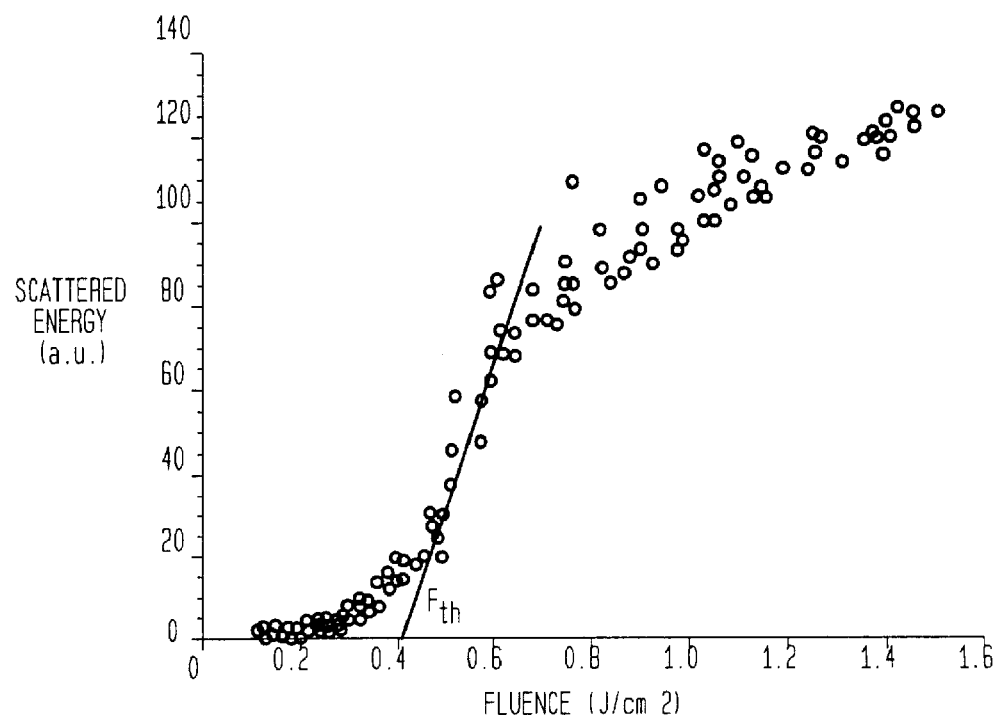
FIG. 2 is a plot of scattered energy versus incident fluence obtained for an opaque (gold) sample using the system in FIG. 1 operated at 150 femtoseconds (fs) pulse duration.
Figure 15:
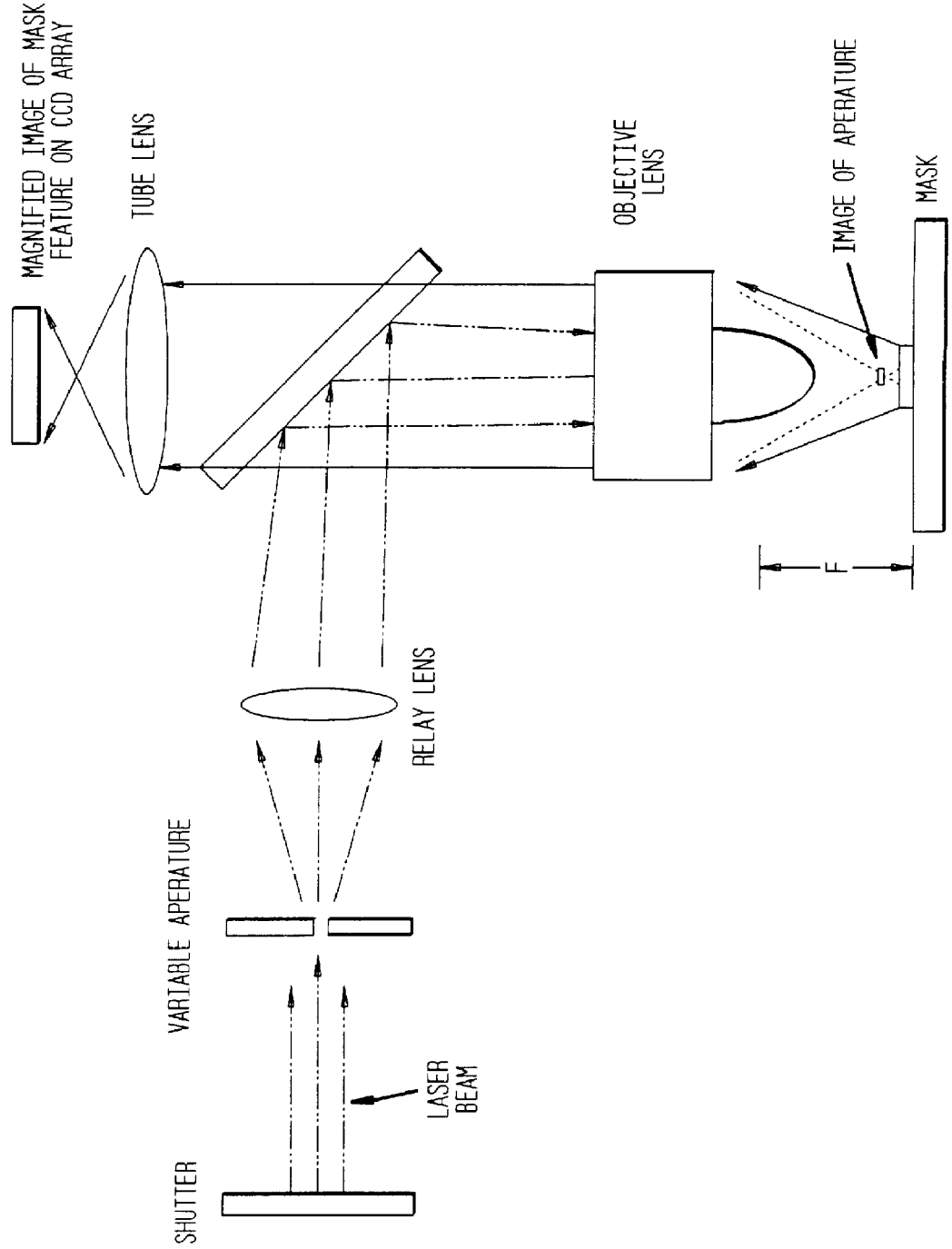
FIG. 15 is an optical system for repairing a photomask. The laser beam illuminates an aperture which is then imaged below the surface of the mask.

There are numerous methods of controlling the focal position of the laser beam which will ensure that the maximum intensity occurs above the surface of the material to be ablated. FIG. 2 shows a schematic diagram of the optical system for repairing chromium defects on a photomask. An objective lens forms an image of the mask on a video camera such as a CCD array. By adjusting the distance (F) between the mask and the objective, the image can be brought into a sharp focus. The optimal distance provides a high quality image of the mask with excellent spatial resolution. This optimal distance can be determined by visually inspecting the sharpness of the image on the CCD array as the distance is varied, using either a computer to perform an analysis of the mask image or manually determining the best focused image. Alternatively, a height sensor can be used to maintain the optimum distance between the mask and the objective lens. The laser beam shown in FIG. 15 illuminates an aperture, which in turn is imaged onto the mask using the relay lens and the mirror. We intentionally adjust the position of the relay lens to ensure that the image of the aperture is focused somewhat above the plane of the mask when the objective lens is adjusted to the optimal imaging distance. Since the objective lens has a large numerical aperture, small variations in the distance between the mask and objective can result in large changes in the effective optical intensity at or below the mask surface. Typically, the uncertainty in the distance F shown in FIG. 15 is comparable to the depth of focus of the optical system. The depth of focus (D) is related to the wavelength of the light (W) and the numerical aperture of the objective lens (NA), and is given approximately by:

$$D \sim W/(2*(NA)^2)$$

We adjust the position of relay lens to form an image of the aperture a distance slightly greater than D above the plane of the mask, with the mask image at best focus. For the mask repair tool we constructed, the numerical aperture is approximately 0.95 and the wavelength of light is 400 nm. Using the method described above, we would typically form an image of the aperture approximately 300 nm above the plane of the mask. This ensures that the peak optical intensity from the laser beam occurs above the mask rather than at or below the surface of the mask, even in cases where the mask image is slightly out of focus (due to the typical uncertainty in determining the optimum focus). The slight defocus in the aperture image at the mask plane has a negligible effect on the spatial resolution of the ablated region.

Figure 16:
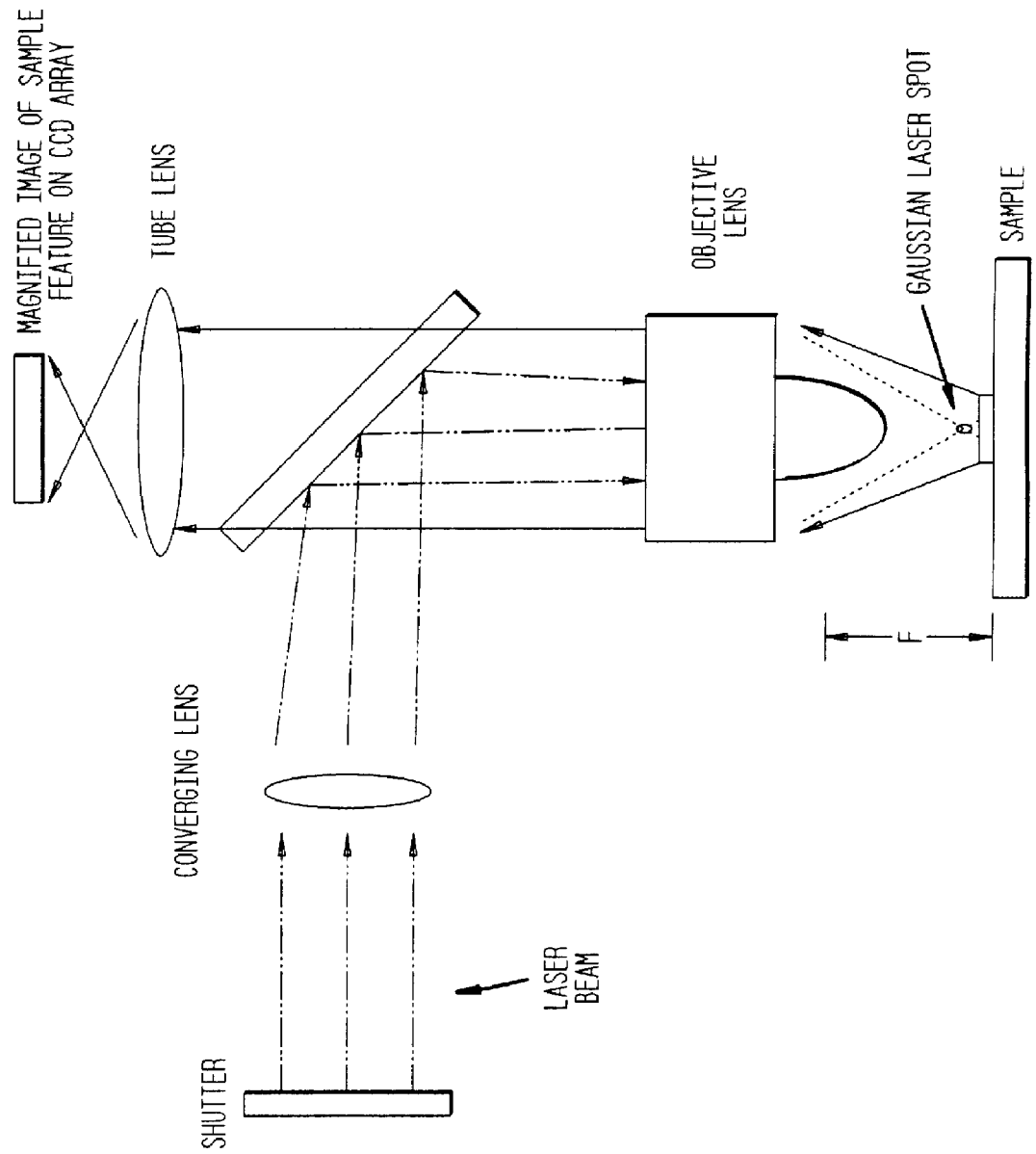
FIG. 16 is a general optical system. A slightly converging laser beam is focused to a gaussian spot slightly above the plane of the mask.

A more general optical approach is shown in FIG. 16. As in the case described above, the distance (F) between the objective lens and the sample is adjusted to bring the image of the sample to the best focus (highest spatial resolution image). However, in this case the laser beam does not illuminate an aperture. Rather, the entire beam enters the objective lens and is focused to a gaussian spot. By adjusting the convergence angle of the laser beam, either through internal adjustments in the laser or through the use of a weak external lens system, the laser beam is brought to a focus slightly above the surface of the sample. The laser intensity is adjusted independently (using filters or a combination of a waveplate and frequency doubling crystal) to a value such that ablation just occurs at the sample surface. Since the peak laser intensity occurs above the surface of the sample rather than inside the sample, the possibility of ablation or damage to the underlying material in the substrate is minimized.

In both cases described above, the focus of the laser beam above the surface of the sample can be maintained by 1) establishing a fixed offset in the relative focus of the sample image and the laser beam, and 2) maintaining the sample at the optimal distance from the objective by monitoring the sample image and/or a height sensor. If a significant depth of material must be removed (e.g. greater than the depth of focus of the optical system), then the distance between the sample and the objective lens can be continuously varied by monitoring the depth of the ablated material and moving either the objective or the sample in the Z direction.

DETAILED DESCRIPTION OF THE PREFERRED EMBODIMENTS

Figure 14A:
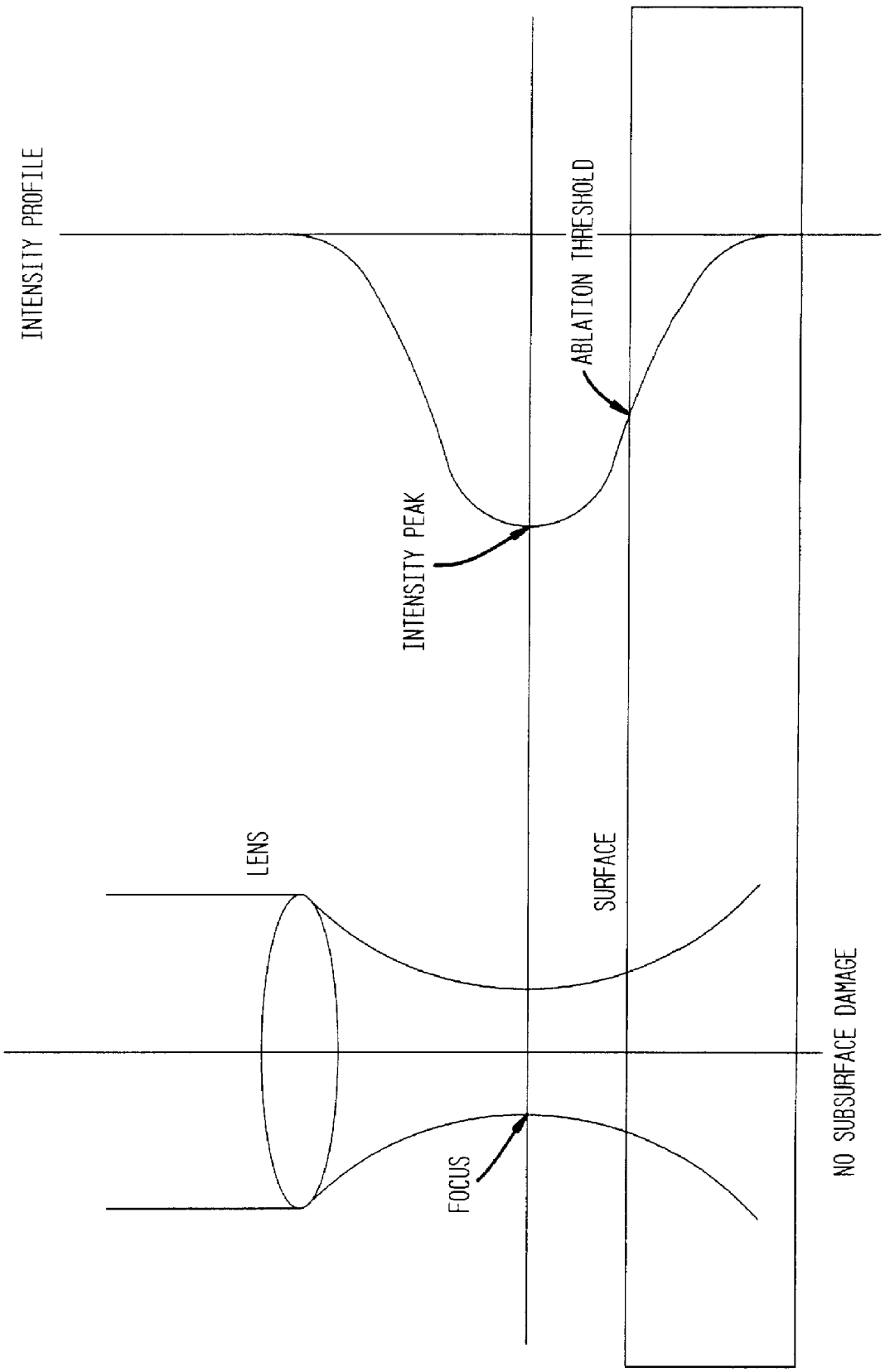
FIG. 14a shows light source focused above the surface to be ablated.

FIG. 14a shows light source focused above the surface of the layer to be ablated.

FIG. 14b shows a light source focused beneath the surface of the layer to be ablated.

FIG. 15 is an optical system for repairing a photomask. The laser beam illuminates an aperture which is then imaged above the surface of the mask.

FIG. 16 is a general optical system. A slightly converging laser beam is focused to a gaussian spot slightly above the plane of the mask.

Referring to FIG. 1 there is shown an apparatus for performing tests to determine the laser induced breakdown threshold as a function of laser pulse width in the nanosecond to femtosecond range using a chirped-pulse amplification (CP A) laser system. The basic configuration of such a CPA system is described in U.S. Pat. No. 5,235,606 which is assigned to the assignee of the present invention and which has inventors in common with this present application. U.S. Pat. No. 5,235,606 is incorporated herein by reference in its entirety.

Chirped-pulse amplification systems have been described by Jeffrey Squier and Gerard Mourou, two of the joint inventors in the present application, in a publication entitled Laser Focus World published by Pennwell in June of 1992. It is described that CPA systems can be roughly divided into four categories. The first includes the high energy low repetition systems such as ND glass lasers with outputs of several joules but they may fire less than 1 shot per minute. A second category are lasers that have an output of approximately 1 joule and repetition rates from 1 to 20 hertz. The third group consists of millijoule level lasers that operate at rates ranging from 1 to 10 kilohertz. A fourth group of lasers operates at 250 to 350 kilohertz and produces a 1 to 2 microjoules per pulse. In U.S. Pat. No. 5,235,606 several solid state amplifying materials are identified and the invention of U.S. Pat. No. 5,235,606 is illustrated using the Alexandrite. The examples below use Ti:Sapphire and generally follow the basic process of U.S. Pat. No. 5,235,606 with some variations as described below.

The illustrative examples described below generally pertain to pulse energies less than a microjoule and often in the nanojoule range with pulse duration in the range of hundreds of picoseconds or less and the frequency on the order of 1 kilohertz. But these examples are merely illustrative and the invention is not limited thereby.

In a basic scheme for CPA, first a short pulse is generated. Ideally the pulse from the oscillator is sufficiently short so that further pulse compression is not necessary. After the pulse is produced it is stretched by a grating pair arranged to provide positive group velocity dispersion. The amount the pulse is stretched depends on the amount of amplification. Below a millijoule, tens of picoseconds are usually sufficient. A first stage of amplification typically takes place in either a regenerative or a multipass amplifier. In one configuration this consists of an optical resonator that contains the gain media, a Pockels cell, and a thin film polarizer. After the regenerative amplification stage the pulse can either be recompressed or further amplified. The compressor consists of a grating or grating pair arranged to provide negative group velocity dispersion. Gratings are used in the compressor to correspond to those in the stretching stage. More particulars of a typical system are described in U.S. Pat. No. 5,235,606, previously incorporated herein by reference.

An important aspect of the invention is the development of a characteristic curve of fluence breakdown threshold Fth as a function of laser pulse width specific to a material. Then identify on such curve, the point at which there is an abrupt, or distinct and rapid change or at least a discernable change in slope characteristic of the material. In general it is more desirable to operate past this point because of the more precise control of the laser induced breakdown (LIB) or ablation threshold.

Example 1

Opaque Material

FIG. 1 shows an experimental setup for determining threshold fluence by determining scattered energy versus incident fluence and by determining threshold fluence versus pulse width. The system includes means for generating a pulsed laser beam as described earlier, and means, typically a lens, for collecting emission from the target to a photomultiplier tube. Change of transmission through a transparent sample is measured with an energy meter.

Figure 3:
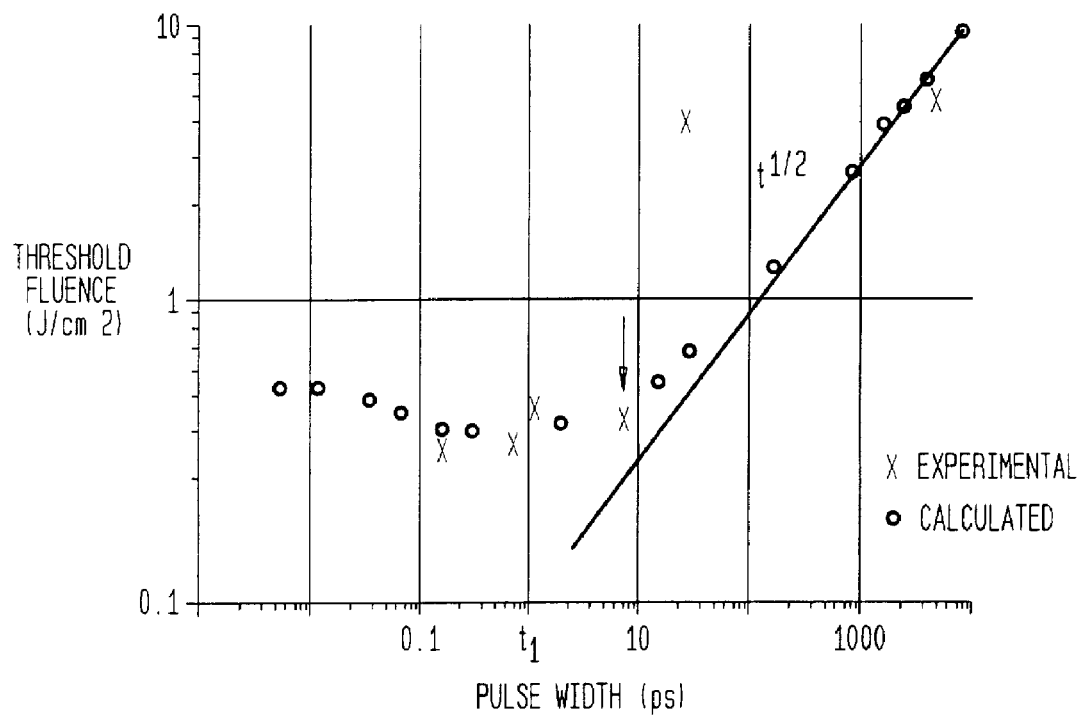
FIG. 3 is a plot of calculated and experimental values of threshold fluence versus pulse width for gold, with experimental values obtained for the gold sample using the system of FIG. 1 operated at 800 nm wavelength. The arrow shows the point on the plot where the Fth proportional to T½ no longer applies, as this relationship only holds for pulse widths down to a certain level as shown by the solid line.

FIG. 2 shows a plot of data obtained from an absorbing medium which is gold using 150 fs pulse and FIG. 3 shows threshold fluence pulse width. The arrow in FIG. 3 identifies the point at which the relationship between the threshold fluence and pulse width varies dramatically.

Figure 4:
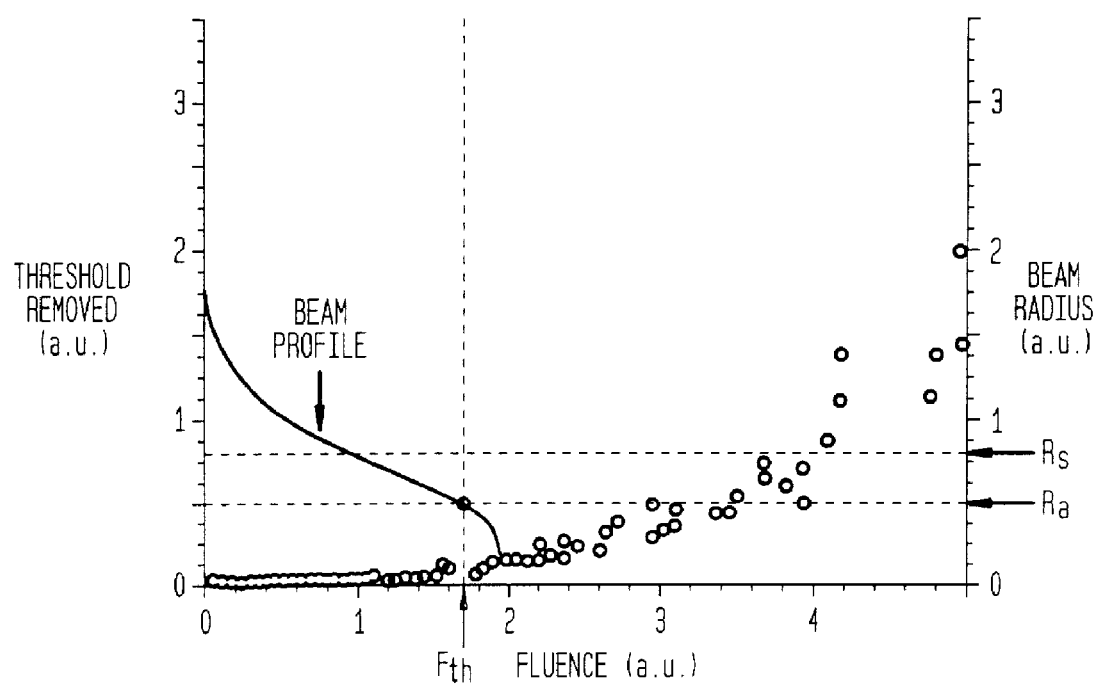
FIG. 4 is a graphical representation of sub-spot size ablation/machining in gold based on arbitrary units and showing Fth the threshold fluence needed to initiate material removal; Rs the spot size of the incident beam and Ra the radius of the ablated hole in the x-y plane.
Figure 5:
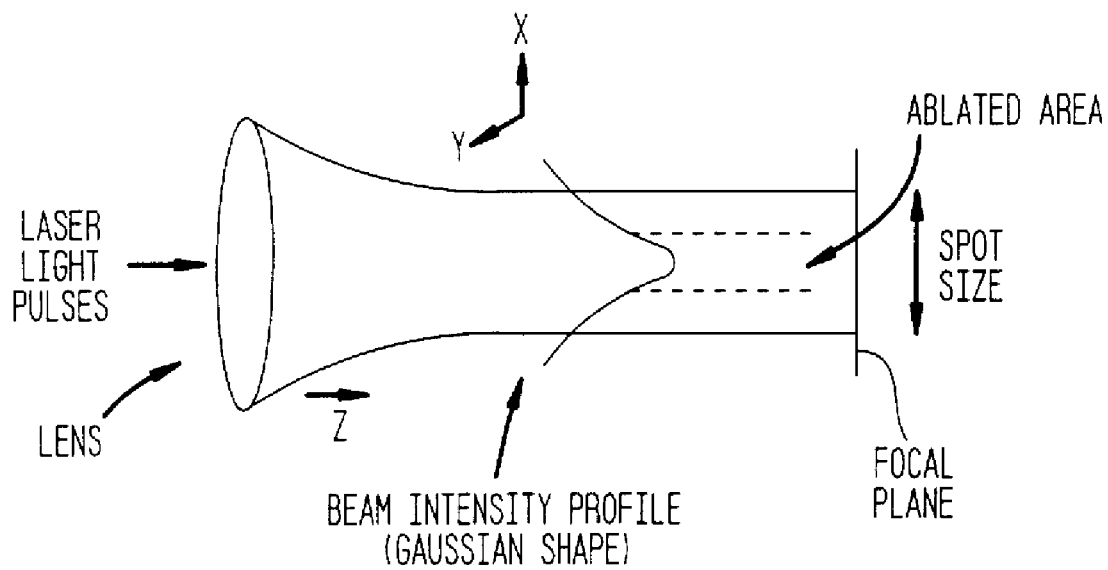
FIG. 5 is a schematic illustration of a beam intensity profile showing that for laser micro-machining with ultrafast pulse according to the invention, only the peak of the beam intensity profile exceeds the threshold intensity for ablation/machining.

In experimental conditions with wavelength of 800 nm and 200 fs pulses on gold (FIG. 3), the absorption depth is 275 A with a diffusion of 50 A. In the case of nanosecond pulses the diffusion length, which is on the order of 10 urn (micron) in diameter, is much longer than the absorption depth, resulting in thermal diffusion being the limiting factor in feature size resolution. Empirical evidence for the existence of these two regimes is as exhibited in FIG. 3. Here both experimental and theoretical ablation thresholds are plotted as a function of pulse width. An arrow at approximately 7 picoseconds pulse width (designated herein as T or .tau.p) delineates the point (or region closely bounding that point) at which the thermal diffusion length (lth) is equal to the absorption depth (I/a). It is clear that for a smaller size spot a shorter (smaller) pulse is necessary. For spot size on the order of 1000 .ANG. or less, pulse width on the order of 100 femtoseconds or less will be needed. It is clear from the figure that this is the point at which the ablation threshold transitions from a slowly varying or nearly constant value as a function of pulse width to one that is dramatically dependent on pulse time. This result is surprising. It has been that the electron thermalization time for laser deposited energy in gold is on the order o£ or less than, 500 fs and the electron-lattice interaction time is 1 ps. The consequences of this for ultrafast laser pulses is that the energy is contained within the beam spot. In fact for energies at or near the threshold for ablation, the spatial profile of the laser beam will determine the size and shape of the region being ablated (FIGS. 4 and 5).

Additional experiments were performed to measure the amount of recombination light produced as a function of the fluence impinging on a gold film. The technique involved is based upon the experimental setup previously described. A basic assumption is that the intensity of the light is proportional to the amount of material ablated. In FIG. 4, the material removed is plotted as a function of fluence. A well defined threshold fluence is observed at which material removal is initiated. By having only a small fraction of the gaussian beam where the fluence is greater than the threshold, the ablated region can be restricted to this small area. In FIG. 4, Ra is the radial position on the beam where the fluence is at threshold. Ablation, then, occurs only within a radius Ra. It is evident that by properly choosing the incident fluence, the ablated spot or hole can in principle be smaller than the spot size, Rs. This concept is shown schematically in FIG. 5. Although the data for a 150 fs pulse is shown in FIG. 4, this threshold behavior is exhibited in a wide range of pulse widths. However, sub spot size ablation is not possible in the longer pulse regimes, due to the dominance of thermal diffusion as will be described below. Additional experiments on opaque materials used a 800 nm Ti:Sapphire oscillator whose pulses were stretched by a grating pair, amplified in a regenerative amplifier operating at 1 kHz, and finally recompressed by another grating pair. Pulse widths from 7 ns to 100 fs were obtained. The beam was focused with a 10* objective, implying a theoretical spot size of 3.0 urn in diameter. A SEM photo-micrograph of ablated holes obtained in a silver film on glass, using a pulse width of 200 fs and a pulse energy of 30 nJ (fluence of 0.4 J/cm2) produced two holes of diameter approximately 0.3 urn in diameter. Similar results have been obtained in aluminum.

These results suggest that by, producing a smaller spot size which is a function of numerical aperture and wavelength, even smaller holes can be machined. We have demonstrated the ability to generate the fourth harmonic (200 nm) using a nonlinear crystal. Thus by using a stronger objective lens along with the 200 nm light, holes with diameters of 200 angstroms could in principle be formed.

These examples show that by using femtosecond pulses the spatial resolution of the ablation/machining process can be considerably less than the wavelength of the laser radiation used to produce it. The ablated holes have an area or diameter less than the area or diameter of the spot size. In the special case of diffraction limited spot size, the ablated hole has a size (diameter) less than the fundamental wavelength size. We have produced laser ablated holes with diameters less than the spot diameter and with diameters 10% or less of the laser beam spot size. For ultrafast pulses in metals the thermal diffusion length, lth=(Dt)l/2 (where D is the thermal diffusivity and t the pulse time), is significantly smaller than the absorption depth (I/a), where a is the absorption coefficient for the radiation.

Those skilled in the art will understand that the basic method of the invention may be utilized in alternative embodiments depending on desired configurations of the induced breakdown. Examples include, but are not limited to using a mask in the beam path, varying spot size, adjusting focus position by moving the lens, adjusting laser cavity design, Fourier Transform (FT) shaping, using a laser operating other than TEMoo, and adjusting the Rayleigh range, the depth of focus or beam waist.

Figure 6A:
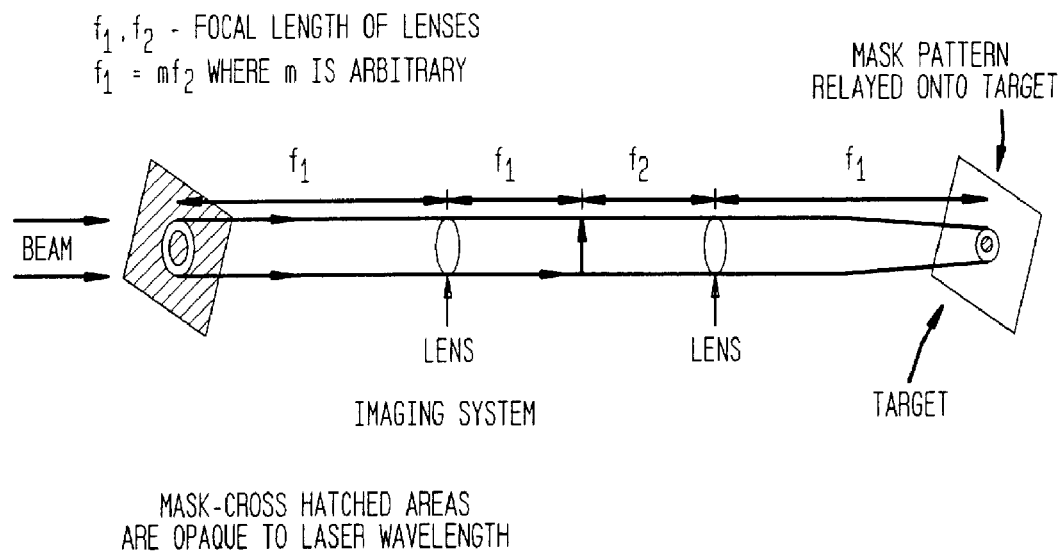
FIGS. 6A and B are schematic illustrations of a beam showing the placement of a disk-shaped mask in the beam path.
Figure 6B:
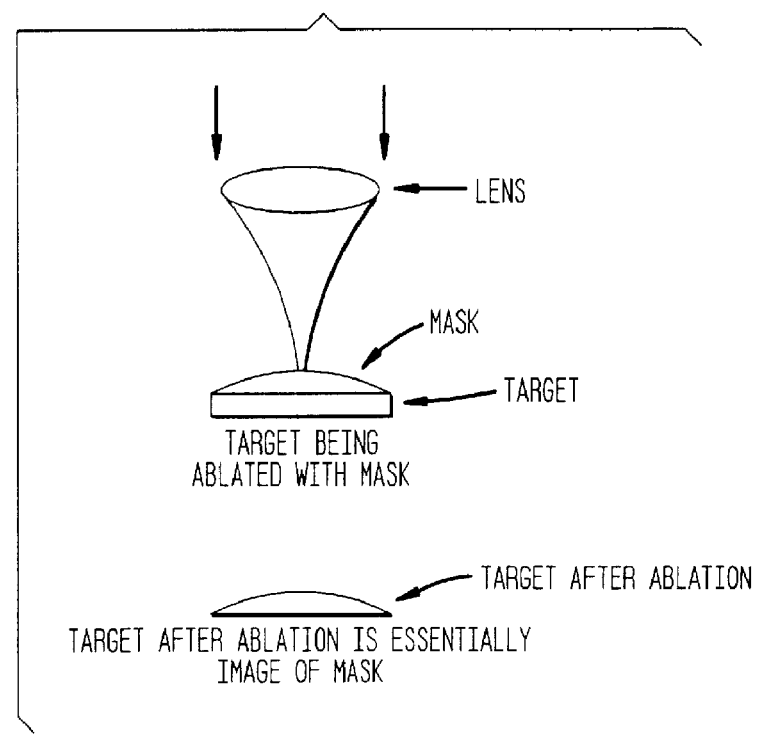

The use of a mask is illustrated in FIGS. 6A and B. The basic method consists of placing a mask in the beam path or on the target itself. If is desired to block a portion of the beam, the mask should be made of an opaque material and be suspended in the beam path (FIG. 6A), the mask may be placed on the target and be absorptive so as to contour the target to the shape of the mask (FIG. 6B).

The varying spot size is accomplished by varying the laster f7#, i.e., varying the focal length of the lens or input beam size to the lens as adjustable diaphragm, in other than the TEMoo mode means that higher order transverse modes could be used. This affects the beam and material as follows: the beam need not be circular or gaussian in intensity. The material will be ablated corresponding to the beam shape.

The Rayleigh range (Z axis) may be adjusted by varying the beam diameter, where the focal plane is in the x-y axis.

Example 2

Transparent Material

A series of tests were performed on an SiO2 (glass) sample to determine the laser induced breakdown (LIB) threshold as a function of pulse width between 150 fs-7 ns, using a CPA laser system. The short pulse laser used was a 10 Hz Ti:Sapphire oscillator amplifier system based on the CPA technique. The laser pulse was focused by an f=25 cm lens inside the SiO2 sample. The Rayleigh length of the beam is ~2 mm. The focused spot size was measured in-situ by a microscope objective lens. The measured spot size FWHM (full at half max) was 26 urn in diameter in a gaussian mode. The fused silica samples were made from Corning 7940, with a thickness of 0.15 mm. They were optically polished on both sides with a scratch/dig of 20-10. Each sample was cleaned by methanol before the. Thin samples were used in order to avoid the complications of self-focusing of the laser pulses in the bulk. The SiO2 sample mounted on a computer controlled motorized X-Y translation stage. Each location on the sample was illuminated by the laser only once.

Figure 7:
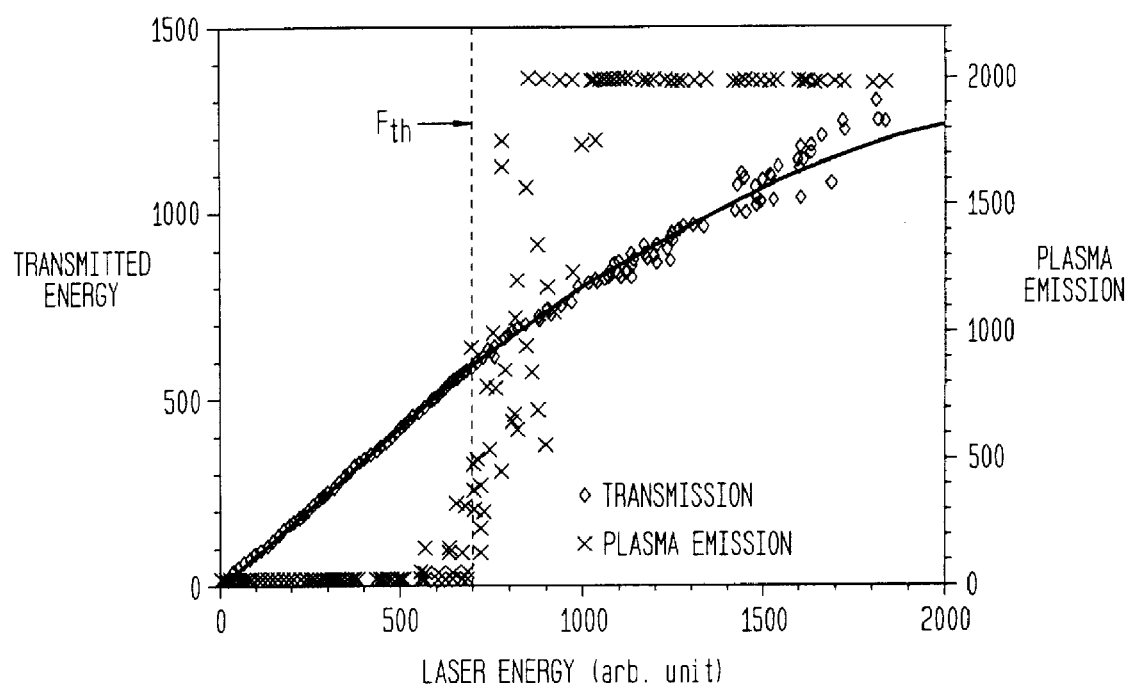
FIG. 7 is a plot of scattered plasma emission and transmitted laser pulse as a function of incident laser pulse energy for a transparent glass sample, SiO2.

Two diagnostics were used to determine the breakdown threshold Fth. First, the plasma emission from the focal region was collected by a lens to a photomultiplier tube with appropriate filters. Second, the change of transmission through the sample was measured with an energy meter. (See FIG. 1) Visual inspection was performed to confirm the breakdown at a nanosecond pulse duration. FIG. 7 shows typical plasma emission and transmitted light signal versus incident laser energy plots, at a laser pulse width of .tau.p=300 fs. It is worth noting that the transmission changed slowly at around Fth. This can be explained by the temporal and spatial behavior of the breakdown with ultrashort pulses. Due to the spatial variation of the intensity, the breakdown will reach threshold at the center of the focus, and because of the short pulse duration, the generated plasma will stay localized. The decrease in transmitted light is due to the reflection, scattering, and absorption by the plasma. By assuming a gaussian profile in both time and space for the laser intensity, and further assuming that the avalanche takes the entire pulse duration to reach threshold, one can show that the transmitted laser energy Ut as a function of the input energy U is given by $$Ut=kU, U<=Uth$$

$$Ut=kUth[1+\ln(U/Uth)], U>Uth$$

where k is the linear transmission coefficient. The solid curve in FIG. 7 is plotted using Eq. (1), with Uth as a fitting parameter. In contrast, breakdown caused by nanosecond laser pulses cuts off the transmitted beam near the peak of the pulses, indicating a different temporal and spatial behavior.

Figure 8:
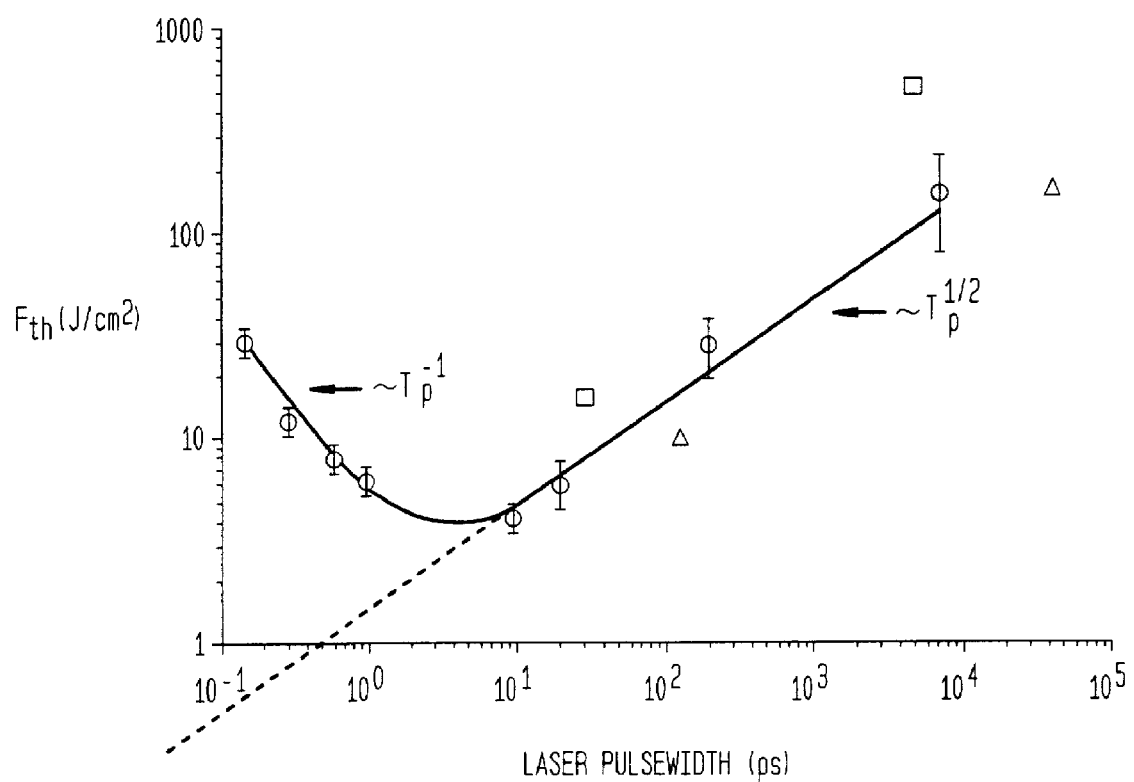
FIG. 8 is a plot of fluence threshold (Fth) versus pulse width (T) for the transparent glass sample of FIG. 7 showing that Fth varying with Tl/2 only holds for pulse widths down to a certain level as shown by the solid line. Previous work of others is shown in the long pulse width regime (Squares, Smith Optical Eng 17, 1978 and Triangles, Stokowski, NBS Spec Bui 541, 1978).

FIG. 8 shows the fluence breakdown threshold Fth as a function of laser pulse width. From 7 ns to about 10 ps, the breakdown threshold the scaling in the relatively long pulse width regime (triangles and squares) are also shown as a comparison—it can be seen that the present data is consistent with earlier work only in the higher pulse width portion of the curve. When the pulse width becomes shorter than a few picoseconds, the threshold starts to increase. As noted earlier with respect to opaque material (metal), this increased precision at shorter pulse widths is surprising. A large increase in damage threshold accuracy is observed, consistent with the multiphoton avalanche breakdown theory. (See FIGS. 8 and 9.) It is possible to make features smaller than spot size in the x-y focal plane and smaller than the Rayleigh range (depth of focus) in the longitudinal direction or Z axis. These elements are essential to making features smaller than spot size or Rayleigh range.

Example 3

Tissue

A series of experiments was performed to determine the breakdown threshold of cornea as a function of laser pulse width between 150 ns, using a CPA laser system. As noted earlier, in this CPA laser system, laser pulse width can be varied while all other experimental parameters (spot size, wavelength, energy, etc.) remain unchanged. The laser was focused to a spot size (FWHM) of 26 ^m in diameter. The plasma emission was recorded as a function of pulse energy in order to determine the tissue damage threshold. Histologic damage was also assessed.

Figure 9:
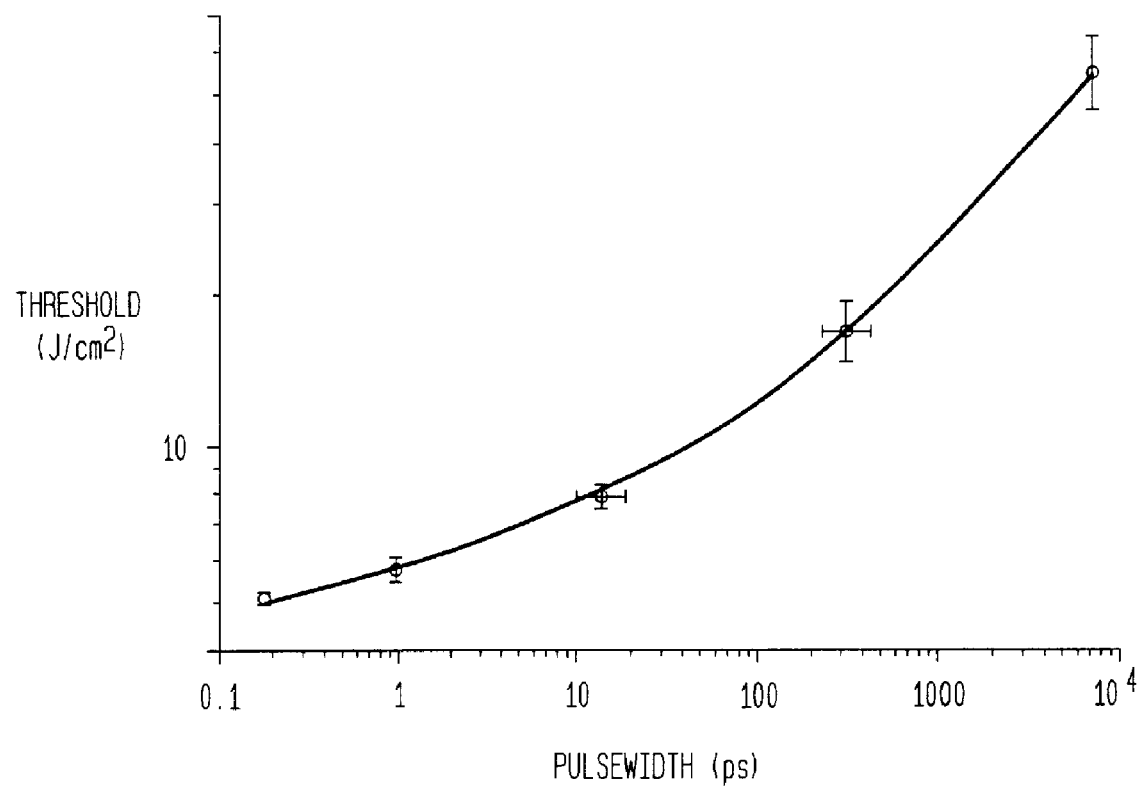
FIG. 9 is a plot of fluence threshold versus pulse width for corneal tissue, again showing that the proportionality between Fth and pulse width follows the Tl/2 relationship only for pulse widths which are relatively long.
Figure 10:
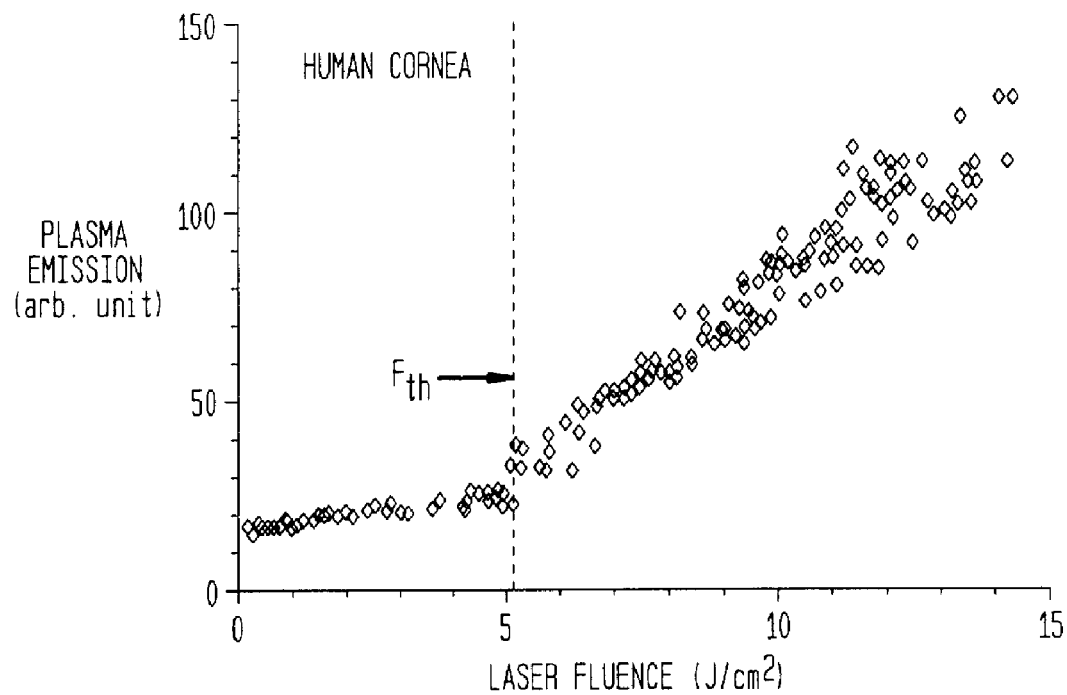
FIGS. 10 and 11 are plots of plasma emission versus laser fluence showing that at 170 (FIG. 10) pulse width the Fth is very clearly defined compared to 7 nm (FIG. 11) pulse width where it is very unclear.
Figure 11:
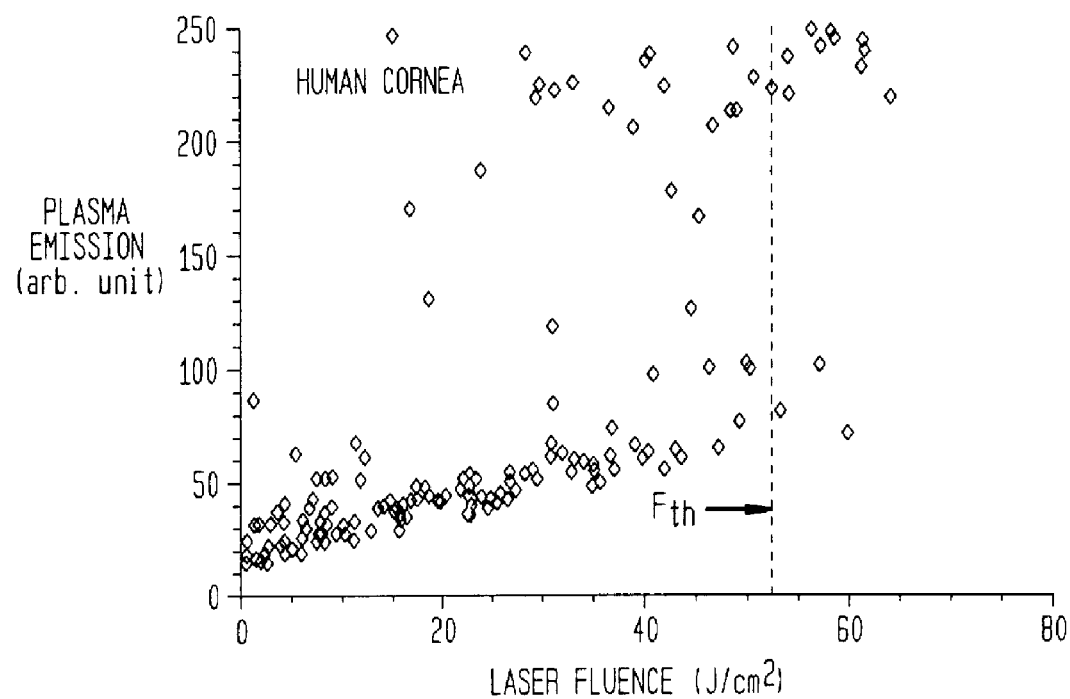

Breakdown thresholds calculated from plasma emission data revealed deviations from the scaling law, Fth .alpha. Tl/2, as in the case of and glass. As shown in FIG. 9, the scaling law of the fluence threshold is true to about 10 ps, and fail when the pulse shortens to less than a few picoseconds. As shown in FIGS. 10 and 11, the ablation or LIB threshold varies dramatically at high (long) pulse width. It is very precise at short pulse width. These results were obtained at 770 nm wavelengths. The standard deviation of breakdown threshold measurements decreased markedly with shorter pulses. Analysis also revealed less adjacent histological damage with pulses less than 10 ps.

The breakdown threshold for ultrashort pulses (<10 ps) is less than longer pulses and has smaller standard deviations. Reduced adjacent histological damage to tissue results from the ultrashort laser pulses.

In summary, it has been demonstrated that sub-wavelength holes can be machined into metal surfaces using femtosecond laser pulses. The effect is physically understood in terms of the thermal diffusion length, over the time period of the pulse deposition, being less than the absorption depth of the incident radiation. The interpretation is further based on the hole diameter being determined by the lateral gaussian distribution of the pulse in relation to the threshold for vaporization and ablation.

Laser induced optical breakdown dielectrics consists of three general steps: free electron generation and multiplication, plasma heating and material deformation or breakdown. Avalanche ionization and multiphoton ionization are the two processes responsible for the breakdown. The laser induced breakdown threshold in dielectric material depends on the pulse width of the laser pulses. An empirical scaling law of the fluence breakdown threshold as a function of the pulse width is given by $F_{th} \alpha \sqrt{\tau_p}$, or alternatively, the intensity breakdown threshold, $I_{th}=F_{th}/\tau_p$. Although this scaling law applies in the pulse width regime from nanosecond to tens of picoseconds, the invention takes advantage of the heretofore unknown regime where breakdown threshold does not follow the scaling law when suitably short laser pulses are used, such as shorter than 7 picoseconds for gold and 10 picoseconds for $SiO_2$.

While not wishing to be held to any particular theory, it is thought that the ionization process of a solid dielectric illuminated by an intense laser pulse can be described by the general equation $dn_e(t)/dt = \eta(E)n_e(t)+(dn_e(t)/dt)PI-(dn_e(t)/dt)loss$ where $n_e(t)$ is the free electron (plasma) density, $\eta(E)$ is the avalanche coefficient, and E is the electric field strength. The second term on the right hand side is the photoionization contribution, and the third term is the loss due to electron diffusion, recombination, etc. When the pulse width is in the picosecond regime, the loss of the electron is negligible during the duration of the short pulse.

Photoionization contribution can be estimated by the tunneling rate. For short pulses, $E-10^8$ V/cm, the tunneling rate is estimated to be $w \sim 4 \times 10^9$ sec$^{-1}$, which is small compared to that of avalanche, which is derived below. However, photoionization can provide the initial electrons needed for the avalanche processes at short pulse widths. For example, the data shows at 1 ps, the rms field threshold is about $5 \times 10^7$ V/cm. The field will reach a value of $3.5 \times 10^7$ V/cm (rms) at 0.5 ps before the peak of the pulse, and $w \sim 100$ sec$^{-1}$. During a $\Delta t \sim 100$ fs period the electron density can reach $n_e \sim n_t[1-\exp(-w\Delta t)] \sim 10^{11}$ cm$^{-3}$, where $n_t \sim 10^{22}$ is the total initial valence band electron density.

Neglecting the last two terms there is the case of an electron avalanche process, with impact ionization by primary electrons driven by the laser field. The electron density is then given by $n_e(t)=n_o \exp(\eta(E)t)$, where $n_o$ is the initial free electron density. These initial electrons may be generated through thermal ionization of shallow traps or photoionization. When assisted by photoionization at short pulse regime, the breakdown is more statistical. According to the condition that breakdown occurs when the electron density exceeds $n_{th} \cong 10^{18}$ cm$^{-3}$ and an initial density of no $\cong 10^{10}$ cm$^{-3}$, the breakdown condition is then given by $\eta \cdot \tau_p$ congruent. 18. For the experiment, it is more appropriate to use $n_{th}$ congruent. $1.6 \times 10^{21}$ cm$^{-3}$, the plasma critical density, hence the threshold is reached when $\eta \cdot \tau_p$ congruent. 30. There is some arbitrariness in the definition of plasma density relating to the breakdown threshold. However, the particular choice of plasma density does not change the dependence of threshold as function of pulse duration (the scaling law).

In the experiment, the applied electric field is on the order of a few tens of MV/cm and higher. Under such a high field, the electrons have an average energy of ~5 eV, and the electron collision time is less than 0.4 fs for electrons with energy $U \gtoreq 5$-6 eV. Electrons will make more than one collision during one period of the electric oscillation. Hence the electric field is essentially a dc field to those high energy electrons. The breakdown field at optical frequencies has been shown to correspond to dc breakdown field by the relationship $E_{rm}\kappa_{th}(w)=E_{dcth}(1+w^2\tau^2)^{1/2}$, where w is the optical frequency and $\tau$ is the collision time.

In dc breakdown, the ionization rate per unit length, $\alpha$, is used to describe the avalanche process, with $\eta = \alpha(E)v_{drift}$, where $v_{drift}$ is the drift velocity of electrons. When the electric field is as high as a few MV/cm, the drift velocity of free electrons is saturated and independent of the laser electric field, $v_{drift}$ congruent. $2 \times 10^7$ cm/s.

The ionization rate per unit length of an electron is just $eE/U_i$ times the probability, $P(E)$, that the electron has an energy $\gtoreq U_i$, or $\alpha(E)=(eE/U_i)P(E)$. Denoting $E_{kT}, E_p$, and $E_i$ as threshold fields for electrons to overcome the decelerating effects of thermal, phonon, and ionization scattering, respectively. Then the electric field is negligible, $E_{kT}$, so the distribution is essentially thermal, $P(E)$ is simply $\exp(-U_i/kT)$. It has been suggested: $P(E) \sim \exp(-\text{const}/E)$ for $E_{kT} p$; $P(E) \sim \exp(-\text{const}/E^2)$ at higher fields $(E > E_p)$. Combining the three cases the expression that satisfies both low and high field limits:

$$\alpha(E)=(eE/U_i)\exp(-E_i/(E(1+E/E_p)+E_{kT}))$$

This leads to $F_{th} \alpha E^2 \tau_p \sim 1/\tau_p$, i.e., the fluence threshold will increase for ultrashort laser pulses when $E > \sqrt{E_p E_i}$ is satisfied.

Figure 12:
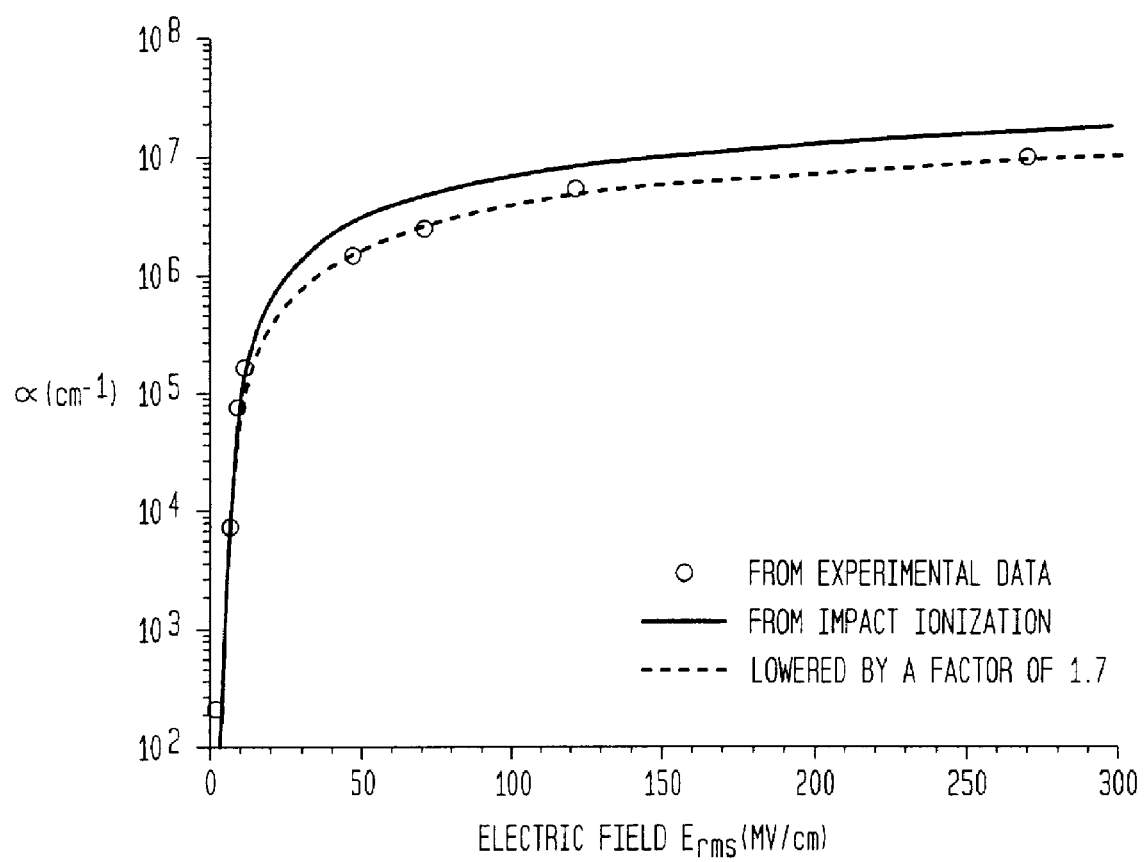
FIG. 12 is a plot of impact ionization rate per unit distance determined by experiment and theoretical calculation.

FIG. 12 is a plot of $\alpha$ as a function of the electric field, E. From experimental data, calculated according to $\eta \cdot \tau_p=30$ and $\eta = \alpha v_{drift}$. The solid curve is calculated from the above equation, using $E_i=30$ MV/cm, $E_p=3.2$ MV/cm, and $E_{kT}=0.01$ MV/cm.

These parameters are calculated from $U=eEl$, where U is the appropriate thermal, phonon, and ionization energy, and l is the correspondent energy relation length ($l_{kT}=l_p \sim 5$ ÅNG., the atomic spacing, and $l_i$ congruent. 30 ÅNG.). It shows the same saturation as the experimental data. The dashed line is corrected by a factor of 1.7, which results in an excellent fit with the experimental data. This factor of 1.7 is of relatively minor importance, as it can be due to a systematic correction, or because breakdown occurred on the surface first, which could have a lower threshold. The uncertainty of the saturation value of $v_{drift}$ also can be a factor. The most important aspect is that the shape (slope) of the curve given by the equation provides excellent agreement with the experimental data. Thus, the mechanism of laser induced breakdown in fused silica (Example 2), using pulses as short as 150 fs and wavelength at 780 nm, is likely still dominated by the avalanche process.

Figure 13A:
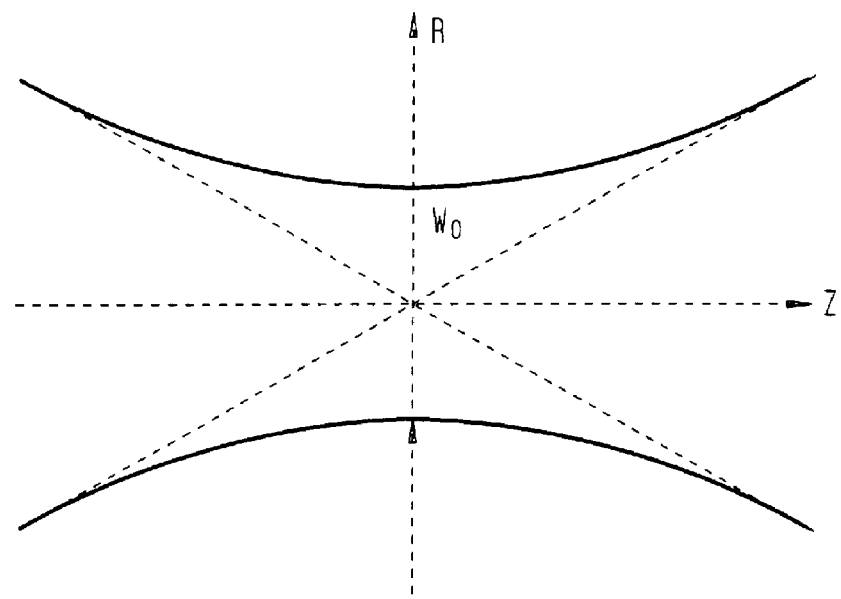
FIGS. 13A and B are schematic illustrations of beam profile along the longitudinal Z axis and sharing precise control of damage-dimension along the Z axis.
Figure 13B:
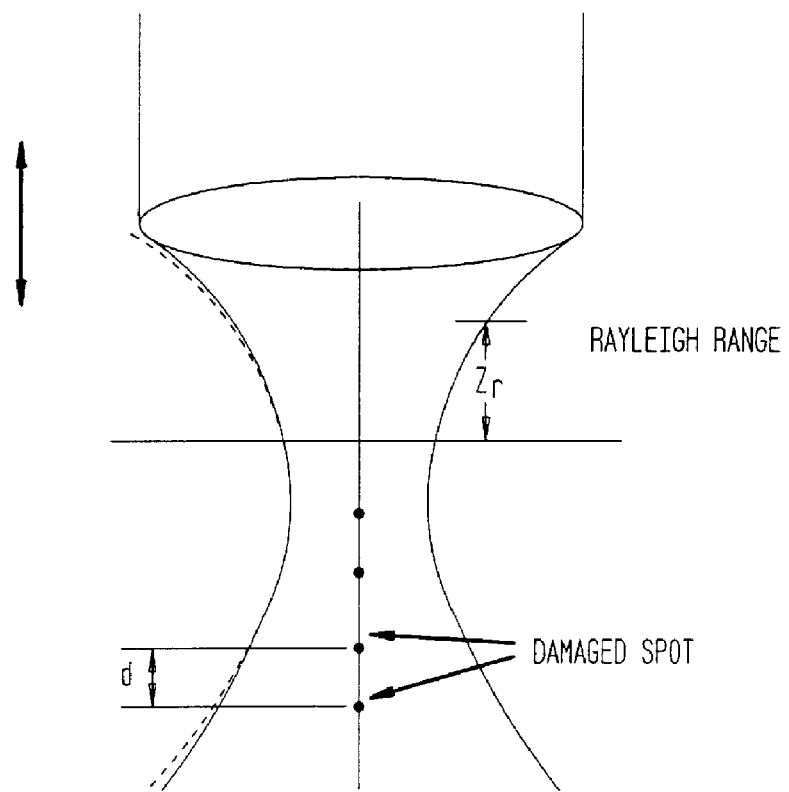

Opaque and transparent materials have common characteristics in the curves of FIGS. 3, 8, and 9 each begins with $F_{th}$ versus $T^{1/2}$ behavior but then distinct change from that behavior is evident. From the point of deviation, each curve is not necessarily the same since the materials differ. The physical characteristics of each material differ requiring a material specific analysis. In the case of SiO2 FIG. 8) the energy deposition mechanism is by dielectric breakdown. The optical radiation is releasing electrons by multiphoton ionization (M PI) that are tightly bound and then accelerating them to higher energies by high field of the laser. It is thought that only a small amount of relatively high energy electrons exist prior to the laser action. The electrons in turn collide with other bound electrons and release them in the avalanching process. In the case of metal, free electrons are available and instantly absorbing and redistributing energy. For any material, as the pulses get shorter laser induced breakdown (LIB) or ablation occurs only in the area where the laser intensity exceeds LIB or ablation threshold. There is essentially insufficient time for the surrounding area to react thermally. As pulses get shorter, vapor from the ablated material comes off after the deposition of the pulse, rather than during deposition, because the pulse duration is so short. In summary, by the method of the invention, laser induced breakdown of a material causes thermal-physical changes through ionization, free electron multiplication, dielectric breakdown, plasma formation, other thermal-physical changes in state, such as melting and vaporization, leading to an irreversible change in the material. It was also observed that the laser intensity also varies along the propagation axis (FIG. 13). The beam intensity as a function of R and Z expressed as:

$$I((Z,R)=Io/(1+Z/ZR)2.\text{multidot.}\exp(-2R2AV2z)$$

where ZR is the Rayleigh range and is equal to [Figure] Wo is the beam size at the waist (Z=0).

We can see that the highest value of the field is at Z=R=0 at the center of the waist. If the threshold is precisely defined it is possible to damage the material precisely at the waist and have a damaged volume representing only a fraction of the waist in the R direction or in the Z direction. It is very important to control precisely the damage threshold or the laser intensity fluctuation.

For example, if the damage threshold or the laser fluctuations known within 10% that means that on the axis (R=0) I(0,Z)/Io=1/(1=(Z/ZR)2=0.9 damaged volume can be produced at a distance ZR/3 where ZR again is the Rayleigh range. For a beam waist of Wo=.lambda, then Figure] and the d distance between hole can [Figure] as shown in FIG. 13.

The maximum intensity is exactly at the center of the beam waist (Z=0, R=0). For a sharp threshold it is possible to damage transparent, dielectric material in a small volume centered around the origin point (Z=0, R=0). The damage would be much smaller than the beam waist in the R direction. Small cavities, holes, or damage can have dimensions smaller than the Rayleigh range (ZR) in the volume of the transparent, dielectric material. In another variation, the lens can be moved to increase the size of the hole or cavity in the Z dimension. In this case, the focal point is essentially moved along the Z axis to increase the longitudinal dimension of the hole or cavity. These features are important to the applications described above and to related applications such as micro machining, integrated circuit manufacture, and encoding data in data storage media.

Advantageously, the invention identifies the regime where breakdown threshold fluence does not follow the scaling law and makes use of such regime to provide greater precision of laser induced breakdown, and to induce breakdown in a preselected pattern in a material or on a material. The invention makes it possible to operate the laser where the breakdown or ablation threshold becomes essentially accurate. The accuracy can be clearly seen by the I-bars along the curves of FIGS. 8 and 9. The I-bars consistently show lesser deviation and correspondingly greater accuracy in the regime at or below the predetermined pulse width.

While this invention has been described in terms of certain embodiment thereof, it is not intended that it be limited to the above description, but rather only to the extent set forth in the following claims. The embodiments of the invention in which an exclusive property or privilege is claimed are defined in the appended claims.

The teaching of the following references are incorporated herein by reference:

Foreign References

| Publication Number | Country | Date |
|---|---|---|
| IPC Class DE04119024A1 | Germany | December 1992 |
| WO08908529 | World Intellectual Property Organization (WIPO) | March 1989 |

Other References

C. V. Shank, R. Yen, and C. Hirlimann, "Time-Resolved Reflectivity Measures of Femtosecond-Optical-Pulse-Induced Phase Transitions in Silicon", Physical Review Letters, vol. 50, No. 6, 454-457, Feb. 7, 1983.

C. V Shank, R. Yen, and C. Hirlimann, "Femtosecnd-Time-Resolved Surface Structural Dynamics of Optically Excited Silicon", Physical Review Letters, vol. 51, No. 10, 900-902, Sep. 5, 1983.

C. V. Shank and M. C. Downer, "Femtosecond Dynamics of Highly Excited Semiconductors", Mat. Res. Soc. Symp. Proc, vol. 51, 15-23, 1985.

S. Kuper and M. Stuke, "Femtosecond uv Excimer Laser Ablation", Applied Physics B, vol. 44, 199-204, 1987.

S. Preuss, M. Spath, Y. Zhang, and M. Stuke, "Time Resolved Dynamics of Subpicosecond Laser Ablation", Applied Physics Letters, vol. 62, No. 23, 3049-3051, Jun. 7, 1993.

A. M. Malvezzi, N. Bloembergen, and C. Y. Huang, "Time-Resolved Picosecond Optical Measurements of Laser-Excited Graphite", Review Letters, vol. 57, No. 1, 146-149, Jul. 7, 1986.

D. H. Reitze, X. Wang, H. Ahn, and M. C. Downer, "Femtosecond Laser Melting of Graphite", Physical Review B, vol. 40, No. 17, Dec. 15, 1989.

F. Muller, K. Mann, P. Simon, J. S. Bernstein, and G. J. Zaal, "A Comparative Study of Decomposition of Thin Films by Laser Induced PVD with Femtosecond and Nanosecond Laser Pulses", SPIE, vol. 1858, 464-475, 1993. International Search Report Form PCT/ISA/210 Dated 31 Jul. 1995 and Mailed 4 Aug. 1995.

M. W. Berns et al., "Laser Microsurgery in Cell and Developmental Biology", Science, vol. 213, No. 31, 505-513, July 1981.

G. L. LeCarpentier et al., "Continuous Wave Laser Ablation of Tissue: Analysis of Thermal and Mechanical Events", IEEE Transactions on Biomedical Engineering, vol. 40, No. 2, 188-200, February 1993.

C. LeBlanc, "Realization and Characterization of a High Intensity Femtosecond Laser System Based on all Titanium Doped Sapphire", Annales de Physique, vol. 19, No. 1, Abstract, February 1994.

R. Birngruber, C. Puliafito, A. Gawande, W. Lin, R. Schoenlein, and J. Fujimoto, "Femtosecond Laser-Tissue Interactions: Retinal Injury Studies", IEEE Journal of Quantum Electronics, vol. QE-23, No. 10, 1836-1844, October 1987.

B. Zysset, J. Fujimoto, and T. Deutsch, "Time-Resolved Measurements of Picosecond Optical Breakdown", Applied Physics B 48, 139-147 (1989).

B. Zysset, J. Fujimoto, C. Puliafito, R Birngruber, and T. Deutsch, "Picosecond Optical Breakdown: Tissue Effects and Reduction of Collateral Damage", Lasers in Surgery and Medicine 9:192-204(1989).

S. Watanabe, R. Anderson, S. Brorson, G. Dalickas, J. Fujimoto, and T. Flotte, "Comparative Studies of Femtosecond to Microsecond Laser Pulses on Selective Pigmented Cell Injury in Skin", Photochemistry and Photobiology vol. 53, No. 6, 757-762, 1991).

N. Bloembergen, "Laser-Induced Electric Breakdown in Solids", IEEE Journal of Quantum Electronics, vol. QE-10, No. 3, (March 1974).

R Birngruber, C. Puliafito, A. Gawande, W. Lin, R. Schoenlein, and J. Fujimoto, "Femtosecond Laser-Tissue Interactions: Retinal Injury Studies", IEEE Log No. 8716039, (1987).

D. Stern, R. Schoenlein, C. Puliafito, E. Dobi, R. Birngruber, and J. Fujimoto, "Corneal Ablation by Nanosecond, Picosecond, and Femtosecond Lasers at 532 and 625 nm", Arch Ophthalmol, vol. 107, (April 1989).

J. Squier, F. Salin, and G. Mourou, "100-fs Pulse Generation and Amplification in Ti:A12 03", Optics letters, vol. 16, No. 5, (March 1991).

B. Frueh, J. Bille, and S. Brown, "Intrastromal Relaxing Excisions in Rabbits with a Picosecond Infrared Laser", Lasers and Light in Ophthalmology, vol. 4, No. 3/4, (1992), 165-168

R. Remmel, C. Dardenne, and J. Bille, "Intrastromal Tissue Removal Using an Infrared Picosecond Nd:YLF Ophthalmic Laser Operating at 1053 nm", Lasers and Light in Ophthalmology, vol. 4, No. 3/4, 169-173, (1992).

J. Squier and G. Mourou, "Tunable Solid-State Lasers Create Ultrashort Pulses", Laser Focus World, (June 1992).

M. H. Niemz, T. P. Hoppeler, T. Juhasz, and J. Bille, "Intrastromal Ablations for Refractive Corneal Surgery Using Picosecond Infrared Laser Pulses", Lasers and Light in Ophthalmology, vol. 5, No. 3, pp. 149-155 (1993).

H. Cooper, J. Schuman, C. Puliafito, D. McCarthy, W. Woods, N. Friedman, N. Wang, and C. Lin, "Picosecond Neodymium:Yttrium Lithium Fluoride Laser Sclerectomy", Am. Journal of Opth. 115:221-224, (February 1993).

K. Frederickson, W. White, R. Wheeland, and D. Slaughter, "Precise Ablation of Skin with Reduced Collateral Damage Using the Femtosecond-Pulsed, Terawatt Titanium-Sapphire Laser", Arch Dermatol, vol. 129, (August 1993).

H. Kapteyn and M. Murnane, "Femtosecond Lasers: The Next Generation", Optics & Photonics News, (March 1994).

G. Mourou, A. Zewail, P. Barbara, and W. Knox, "New Generation of Ultrafast Sources Marked by Higher Powers, Versality", Optics Photonics News, (March 1994).

D. Du, X. Liu, G. Korn, J. Squier, and G. Mourou, "Laser-Induced Breakdown by Impact Ionization in SiO2 with Pulse Widths from 7 ns to 150 fs", Appl. Phys. Lett 64 (23), (Jun. 6, 1994).

Optics, Eugene Hecht et al., Addison-Wesley Publishing Company, 1979.

The teachings of the following United States patents (US Patents); World Intellectual Property Organization patents (WO Patents); Japanese patents (JP Patents); European Patent Office patents (EP Patents) and patents of other foreign jurisdictions (DD, DE, GB, RU, SU) are incorporated herein by reference. The methods and apparatus described herein can be advantageously utilized in the methods and apparatus of the incorporated references to achieve the enhanced properties and features described herein in the methods and apparatus of the incorporated references. For example where the reference uses a radiation beam, such as a light beam, in-particular a laser beam, the laser techniques according to the present invention can be used. The laser pulse of the present invention can be directed for example by using a light pipe or a wave guide. Commonly available, such as commercially available, light pipes and wave guides can be used.

| U.S. Pat. Nos. | | | | | |
|---|---|---|---|---|---|
| 6,251,102 | 6,238,386 | 6,231,568 | 6,231,567 | 6,224,589 | 6,213,998 |
| 6,200,311 | 6,190,377 | 6,152,919 | 6,066,127 | 5,951,543 | 5,893,828 |
| 5,868,731 | 5,860,426 | 5,783,798 | 5,725,523 | 5,688,263 | 5,658,275 |
| 5,611,797 | 5,607,420 | 5,571,098 | 5,562,658 | 5,549,600 | 5,534,000 |
| 5,454,808 | 5,403,306 | 5,397,327 | 5,366,456 | 5,346,489 | 5,312,396 |
| 5,290,279 | 5,269,778 | 5,224,942 | 5,219,347 | 5,195,541 | 5,194,712 |
| 5,180,378 | 5,163,935 | 5,154,708 | 5,125,923 | 5,098,427 | 5,092,864 |
| 5,074,861 | 5,004,338 | 4,963,143 | 4,950,268 | 4,939,336 | 4,862,886 |
| 4,846,171 | 4,832,979 | 4,812,613 | 4,791,927 | 4,791,926 | 4,790,310 |
| 4,788,975 | 4,736,743 | 4,729,373 | 4,702,245 | 4,693,244 | 4,669,465 |
| 4,658,817 | 4,638,800 | 4,633,872 | 4,627,435 | 4,597,380 | 4,592,353 |
| 4,580,557 | 4,573,466 | 4,573,465 | 4,566,453 | 4,564,012 | 4,550,240 |
| 4,532,400 | 4,519,390 | 4,517,973 | 4,503,854 | 4,497,319 | 4,491,131 |
| 4,478,217 | 4,473,074 | 4,470,414 | 4,469,098 | 4,459,986 | 4,408,602 |
| 4,273,109 | 4,270,845 | 4,266,549 | 4,266,548 | 4,266,547 | 4,249,533 |
| 4,240,431 | 4,233,493 | 4,185,633 | 4,174,154 | 4,144,888 | 4,143,660 |
| 4,141,362 | 3,910,276 | 3,906,953 | 3,865,114 | 3,865,113 | 3,858,577 |
| 3,123,066 | | | | | |

| WO patents | | | | | |
|---|---|---|---|---|---|
| 0,141,871 | 0,128,447 | 0,110,304 | 0,115,592 | 0,113,812 | 0,113,810 |
| 0,106,908 | 0,019,920 | 0,110,288 | 0,108,576 | 0,108,579 | 0,078,242 |
| 0,054,686 | 0,048,525 | 9,965,405 | 9,955,243 | 9,955,218 | 9,951,156 |
| 9,944,518 | 9,900,062 | 9,818,394 | 9,713,468 | 9,715,236 | 9,612,441 |
| 9,410,923 | 9,325,156 | 9,314,432 | 9,312,727 | 9,311,699 | 9,221,299 |
| 9,217,138 | 9,208,427 | 9,206,641 | 9,203,977 | 9,012,619 | 8,704,610 |
| 8,606,642 | 8,505,263 | 8,505,262 | 8,500,010 | | |

| JP patents | | | |
|---|---|---|---|
| 2001054524 | 2001029359 | 2001008946 | 2001008945 |
| 11104147 | 10328196 | 10113354 | 08229049 |
| 09010221 | 09000537 | 08299352 | 08148737 |
| 07124169 | 06090959 | 05220167 | 05220166 |
| 05220101 | 05176938 | 04023339 | 04129545 |
| 03278489 | 03139346 | 03041943 | 02239857 |
| 02099048 | 01320050 | 01036650 | 01034347 |
| 63318935 | 60104902 | 59195891 | 58145901 |
| 58087887 | 58084887 | 56114390 | 55083011 |
| 55083010 | | | |

| EP patents |
|---|
| 1097676 |
| 0717964 |
| 0669107 |
| 0423431 |
| 0458506 |
| 0391976 |

-continued

| EP patents |
| --- |
| 0372362 |
| 0327410 |
| 0341943 |
| 0297360 |
| 0292622 |
| 0069351 |

| Other patents |
| --- |
| DD217711 |
| DD258360 |
| DE2646029 |
| DE4030240 |
| GB2214084 |
| GB2274724 |
| RU2113827 |
| RU2090157 |
| RU2077274 |
| RU2045935 |
| STJ570233 |

We claim:

1. A method of removal of a first biological tissue from the surface of a second biological tissue using laser induced breakdown of the first biological tissue which comprises:
    a. generating a beam of one or more laser pulses in which each pulse has a pulse width equal to or less than a pulse width value corresponding to a change in slope of, a curve of fluence breakdown threshold (Fth) as a function of laser pulse width (T), said change occurring at a point between first and second portions of said curve, said first portion spanning a range of relatively long pulse width where Fth varies with the square root of pulse width (T1/2) and said second portion spanning a range of short pulse width relative to said first portion with a Fth versus T slope which differs from that of said first portion; and
    b. focusing said one or more pulses of said beam to a point above the surface of the first biological tissue.

2. The method according to claim 1 and further including:
    a. identifying a pulse width start point;
    b. focusing the laser beam initial start point above the surface of the tissue; and
    c. scanning said beam along a predetermined path in a transverse direction.

3. The method according to claim 1 and further including:
    a. identifying a pulse width start point;
    b. focusing the laser beam initial start point above the surface of the tissue; and
    c. scanning said beam along a predetermined path in a longitudinal direction in the tissue to a depth smaller than the Rayleigh range.

4. The method according to claim 1 wherein the breakdown includes changes caused by one or more of ionization, free electron multiplication dielectric breakdown, plasma formation and vaporization.

5. The method according to claim 1 wherein the breakdown includes plasma formation.

6. The method acct ding to claim 1 wherein the breakdown includes disintegration.

7. The method according to claim 1 wherein the breakdown includes ablation.

8. The method according to claim 1 wherein the breakdown includes vaporization.

9. The method according to claim 1 wherein said beam is obtained by chirped-pulse amplification (CPA) means comprising means for generating a short optical pulse having a predetermined duration; means for stretching such optical pulse in time; means for amplifying such time-stretched optical pulse including solid state amplifying media; and means for recompressing such amplified pulse to its original duration.

10. A method of removal of a first biological tissue from the surface of a second biological tissue using laser induced breakdown (LIB) of a tissue with a pulsed laser beam, the tissue being characterized by a relationship of fluence breakdown threshold versus laser pulse width that exhibits a rapid and distinct change in slope at a predetermined laser pulse width where the onset of plasma induced breakdown occurs, said method comprising the steps of:
    a. generating a beam of one or more laser pulses in which each pulse has a pulse width equal to or less than said predetermined laser pulse width; and
    b. focusing said beam to a point above the surface of the first biological tissue material so that the laser beam defines a spot and has a lateral gaussian profile characterized in that fluence at or near the center of the beam spot is greater than the threshold fluence whereby the laser induced breakdown is ablation of an area within the spot.

11. The method according to claim 10 wherein the spot size is a diffraction limited spot size providing an ablation cavity having a diameter less than the fundamental wavelength size.

12. A method for laser induced breakdown (LIB) of a tissue with a pulsed laser beam, the tissue being characterized by a relationship of fluence breakdown threshold versus laser pulse width that exhibits a rapid and distinct change in slope at a predetermined laser pulse width where the onset of plasma induced breakdown occurs, said method comprising the steps of:
    a. generating a beam of one or more laser pulses in which each pulse has a pulse width equal to or less than said predetermined laser pulse width; and
    b. focusing said beam to a point above the surface of the tissue which is biological tissue, the pulse width is 10 to 10,000 femtoseconds and the beam has an energy of 10 nanojoules to 1 millijoule.

13. A method according to claim 12 wherein said point is moved as said tissue is removed from said surface so that said point is substantially maintained at a fixed distance above said ablated surface.

14. A method for laser induced breakdown of a first biological tissue on a second biological tissue which comprises:
    a. determining, for a selected tissue, a characteristic curve of fluence breakdown threshold (Fth) as a function of laser pulse width;
    b. identifying a pulse width value on said curve corresponding to a rapid and distinct change in slope of said Fth versus pulse width curve characteristic of said tissue;
    c. generating a beam of one or more laser pulses, said having a pulse width at or below said pulse width value corresponding to said distinct change in slope; and
    d. focusing said one or more pulses of said beam to a point above the surface of the first biological tissue.

15. The method according to claim 14 and further including:
    a. identifying a pulse width start point;
    b. focusing the laser beam initial start point at or beneath the surface of the first biological tissue; and c. mining said beam along a predetermined path in a transverse direction.

16. The method according to claim 14 and further including:
   a. identifying a pulse width start point;
   b. focusing the laser beam initial start point above the surface of the tissue; and
   c. scanning said beam along a predetermined path in a longitudinal direction in the tissue to a depth smaller than the Rayleigh range.

17. The method according to claim 14 wherein the breakdown includes changes caused by one or more of ionization, free electron multiplication, dielectric breakdown, plasma formation, and vaporization.

18. The method according to claim 14 wherein the breakdown includes plasma formation.

19. The method according to claim 14 wherein the breakdown includes disintegration.

20. The method according to claim 14 wherein the breakdown include ablation.

21. The method according to claim 14 wherein breakdown includes vaporization.

22. The method according to any one of claim 12, or 14 wherein said beam is obtained by chirped-pulse amplification (CPA) means comprising means for generating a short optical pulse having a predetermined duration; means for stretching such optical pulse in time; means for amplifying such time-stretched optical pulse including solid state amplifying media; and means for recompressing such amplified pulse to its original duration.

23. A method according to claim 10, 12, 14 or 15 wherein said laser-induced breakdown removes said first biological tissue from said surface resulting in an ablated surface.

24. A method far laser induced breakdown (LIB) of a first biological tissue on a second biological tissue with a pulsed laser beam, the tissue being characterized by a relationship of fluence breakdown threshold versus laser pulse width that exhibits a rapid and distinct change in slope at a characteristic laser pulse width, said method comprising the steps of:
   a. generating a beam of one or more laser pulses in which each pulse has a pulse width equal to or less than said characteristic laser pulse width; and
   b. focusing said beam to a point above the surface of the first biological tissue.

25. The method according to claim 24 wherein the pulse width is 10 to 10,000 femtoseconds and the beam has an energy of 1 nanojoule to 1 microjoule.

26. The method according to claim 24 wherein the spot size is varied within a range of 1 to 100 microns by changing the f number of the laser beam.

27. The method according to claim 24 wherein the spot size is varied within a range of 1 to 100 microns by varying the target position.

28. The method according to claim 24 wherein the tissue is transparent to radiation emitted by the laser and the pulse width is 10 to 10,000 femtoseconds, the beam has an energy of 10 nanojoules to 1 millijoule.

29. The method according to claim 24 wherein the tissue is biological tissue, the pulse width is 10 to 10,000 femtoseconds and the beam has an energy of 10 nanojoules to 1 millijoule.

30. The method according to claim 24 wherein the laser beam has an energy in a range of 10 nanojoules to 1 millijoule.

31. The method according to claim 24 wherein the laser beam has a fluence in a range of 100 millijoules per square centimeter to 100 joules per square centimeter.

32. The method according to claim 24 wherein the laser beam defines a spot in or on the tissue and the LIB causes ablation of an area having a size smaller than the area of the spot.

33. The method according to claim 24 wherein the laser beam has a wavelength in a range of 200 nanometers to 2 microns.

34. The method according to claim 24 wherein the pulse width is in a range of a few picoseconds to femtoseconds.

35. The method according to claim 24 wherein the breakdown includes changes caused by one or more of ionization, free electron multiplication, dielectric breakdown, plasma formation, and vaporization.

36. The method according to claim 24 wherein the breakdown includes plasma formation.

37. The method according to claim 24 wherein the breakdown includes disintegration.

38. The method according to claim 24 wherein the breakdown includes ablation.

39. The method according to claim 24 wherein the breakdown includes vaporization.

40. The method according to claim 24 wherein the spot size is varied by flexible diaphragm to a range of 1 to 100 microns.

41. The method according to claim 24 wherein a mask is placed in the path of the beam to block a portion of the beam to cause the beam to assume a desired geometric configuration.

42. The method according to claim 24 wherein the laser operating mode is non-TEMoo.

43. The method according to claim 24 wherein the laser beam defines a spot and has a lateral gaussian profile characterized in that fluence at or near the center of the beam spot it greater than the threshold fluence whereby the laser induced breakdown is ablation of an area within the spot.

44. The method according to any one of claim 24, 25, 28 or 38 wherein said beam is obtained by chirped-pulse amplification (CPA) means comprising means for generating a short optical pulse having a predetermined duration; means for stretching such optical pulse in time, means for amplifying such time-stretched optical pulse including solid state amplifying media; and means for recompressing such amplified pulse to its original duration.

45. A method for laser induced breakdown of a first biological tissue on a second biological tissue which comprises:
   a. generating a beam of one or more laser pulses in which each pulse has a pulse width equal to or less than a pulse width value corresponding to a change in slope of a curve of fluence breakdown threshold (Fth) as a function of laser pulse width (T), said change occurring at a point between first and second portions of said curve, said first portion spanning a range of relatively long pulse width where Fth varies with the square root of pulse width (T1/2) and said second portion spanning a range of short pulse width relative to said first portion with a Fth versus T slope which differs from that of said first portion; and
   b. focusing said one or more pulses of said beam to a region of least confusion above the surface of the first biological tissue.

46. The method according to claim 45 and further including:
   a. identifying a pulse width start point;
   b. focusing the laser beam initial start point at or beneath the surface of the first biological tissue; and
   c. scanning said beam along a predetermined path in a transverse direction.

47. The method according to claim 45 and further including:

a. identifying a pulse width start point;
b. focusing the laser beam initial tar point above the surface of the first biological tissue; and
c. scanning said beam along a predetermined path in a longitudinal direction in the tissue to a depth smaller than the Rayleigh ange.

48. The method according to claim 45 wherein the breakdown includes changes caused by one or more of ionization, free electron multiplication, dielectric breakdown, plasma formation, and vaporization.

49. The method according to claim 45 wherein the breakdown includes plasma formation.

50. The method according to claim 45 wherein the breakdown includes disintegration.

51. The method according to claim 45 wherein the breakdown includes ablation.

52. The method according to claim 45 wherein the breakdown includes vaporization.

53. A method for laser induced breakdown (LIB) of a first biological tissue on a second biological tissue with a pulsed laser bears the tissue being characterized by a relationship of fluence breakdown threshold versus laser pulse width that exhibits a rapid and distinct change in slope at a predetermined laser pulse width where the onset of plasma induced breakdown occurs, said method comprising the steps of:
a. generating a beam of one or more laser pulses in which each pulse has a pulse width equal to or less than said predetermined laser pulse width; and
b. focusing said beam to, a region of least confusion above the surface of the first biological tissue so that the laser beam defines a spot and has a lateral gaussian profile characterized in that fluence at or near the center of the beam spot is greater than the threshold fluence whereby the laser induced breakdown is ablation of an area within the spot.

54. The method according to claim 53 wherein the spot size is a diffraction limited spot size providing an ablation cavity having a diameter less than the fundamental wavelength size.

55. A method for laser induced breakdown (LIB) of a first biological tissue with a pulsed laser beam, the first biological tissue being characterized by a relationship of fluence breakdown threshold versus laser pulse width that exhibits a rapid and distinct change in slope at a predetermined laser pulse width where the onset of plasma induced breakdown occurs, said method comprising the steps of:
a. generating a beam of one or more laser pulses in which each pulse has a pulse width equal to or less than said predetermined laser pulse width; and
b. focusing said beam to a region of east confusion above the surface of the first biological tissue which is biological tissue, the pulse width is 10 to 10,000 femtoseconds and the beam has an energy of 10 nanojoules to 1 millijoule.

56. A method for laser induced breakdown of a first biological tissue on a second biological tissue which comprises:
a. determining, for a selected first biological tissue, a characteristic curve of fluence breakdown threshold (Fth) as a function of laser pulse width;
b. identifying a pulse width value on said curve corresponding to a rapid and distinct change in slope of said Fth versus pulse width curve characteristic of said first biological tissue;
c. generating a beam of one or more laser pulses, said having a pulse width at or below said pulse width value corresponding to said distinct change in slope; and
d. focusing said one or more pulses of said beam to a region of least confusion above the surface of the first biological tissue.

57. The method according to claim 56 and further including:
a. identifying a pulse width start point;
b. focusing the laser beam initial start point at or beneath the surface of the first biological tissue, and
c. scanning said beam along a predetermined path in a transverse direction.

58. The method according to claim 56 and further including:
a. identifying a pulse width start point;
b. focusing the laser beam initial start region of least confusion above the surface of the tissue; and
c. scanning said beam along a predetermined path in a longitudinal direction in the tissue to a depth smaller than the Rayleigh range.

59. The method according to claim 56 wherein the breakdown includes changes caused by one or more of ionization, free electron multiplication, dielectric breakdown, plasma formation, and vaporization.

60. The method according to claim 56 wherein the breakdown includes plasma formation.

61. The method according to claim 56 wherein the breakdown includes disintegration.

62. The method according to claim 56 wherein the breakdown include ablation.

63. The method according to claim 56 wherein breakdown includes vaporization.

64. The method according to any one of claim 55 or 56 wherein said beam is obtained by chirped-pulse amplification (CPA) means comprising means for generating a short optical pulse having a predetermined duration; means for stretching such optical pulse in time; means for amplifying such time-stretched optical pulse including solid state amplifying media; and means for recompressing such amplified pulse to its original duration.

65. A method for laser induced breakdown (LIB) of a first biological tissue on a second biological tissue by plasma formation with a pulsed laser beam, the first biological tissue being characterized by a relationship of fluence breakdown threshold versus laser pulse width that exhibits a distinct change in slope at a characteristic laser pulse width, said method comprising the steps of:
a. generating a beam of one or more laser pulses in which each pulse has a pulse width equal to or less than said characteristic laser pulse width, said characteristic pulse width being defined by the ablation (LIB) threshold of the tissue as a function of pulse width where the ablation (LIB) threshold function is no longer proportional to the square root of pulse width; and
b. focusing said beam to a region of least contusion above the surface of the first biological tissue and inducing breakdown by plasma formation in the first biological tissue.

66. A method according to claim 1, 10, 12, 14, 15, 24, 45, 53, 55, 65, 56 or 57 wherein said first biological tissue is disposed on the second biological tissue.

67. A method according to claim 66 wherein said second biological tissue is the same as said first biological tissue.

68. A method according to claim 66 wherein said second biological tissue is different than said second biological tissue.

69. A method according to claim 66 wherein said second biological tissue is a first tissue and said tissue is a second biological tissue.

70. A method according to claim 69 wherein said first tissue is a tumor and wherein said second tissue is normal tissue.

71. A method according to claim 70 wherein said second tissue is a retina of an eye and said tumor is disposed on said retina.

72. A method according to claim 24, 45, 53, 55, 65, 56 or 57 wherein said laser-induced breakdown removes said first biological tissue from said surface resulting in an ablated surface.

73. A method according to claim 72 wherein said region of least, confusion is moved as said first biological tissue is ablated so that said region of least confusion is substantially maintained at a fixed distance above said ablated surface.

* * * * *